US009233944B2

(12) United States Patent
Subramaniam et al.

(10) Patent No.: US 9,233,944 B2
(45) Date of Patent: Jan. 12, 2016

(54) ALKYLENE EPOXIDATION WITH MESOPOROUS CATALYSTS

(71) Applicant: UNIVERSITY OF KANSAS, Lawrence, KS (US)

(72) Inventors: Bala Subramaniam, Lawrence, KS (US); Anand Ramanathan, Lawrence, KS (US); Madhav Ghanta, Lawrence, KS (US); Wenjuan Yan, Lawrence, KS (US)

(73) Assignee: UNIVERSITY OF KANSAS, Lawrence, KS (US)

(*) Notice: Subject to any disclaimer, the term of this patent is extended or adjusted under 35 U.S.C. 154(b) by 0 days.

(21) Appl. No.: 14/409,503

(22) PCT Filed: Jun. 27, 2013

(86) PCT No.: PCT/US2013/048077
§ 371 (c)(1),
(2) Date: Dec. 19, 2014

(87) PCT Pub. No.: WO2014/004768
PCT Pub. Date: Jan. 3, 2014

(65) Prior Publication Data
US 2015/0191442 A1 Jul. 9, 2015

Related U.S. Application Data

(60) Provisional application No. 61/690,475, filed on Jun. 27, 2012, provisional application No. 61/690,476, filed on Jun. 27, 2012.

(51) Int. Cl.
C07D 301/19 (2006.01)
C07D 301/12 (2006.01)

(52) U.S. Cl.
CPC ............ C07D 301/19 (2013.01); C07D 301/12 (2013.01)

(58) Field of Classification Search
CPC ... C07D 301/12; C07D 303/04; C07D 301/19
USPC .......................................................... 549/529
See application file for complete search history.

(56) References Cited

U.S. PATENT DOCUMENTS 5,430,161 A    7/1995  Brown et al.
5,460,161 A *  10/1995 Englehart et al. ............. 502/317
6,358,486 B1   3/2002  Shan et al.
(Continued)

OTHER PUBLICATIONS

Ghanta, Development of an Economically viable H2O2-based, Liquid Phase Ethylene Oxide Technology (Dissertation; Reactor Engineering and Catalyst Development Studies, University of Kansas, May 2012, p. 1-258.*

(Continued)

Primary Examiner — T. Victor Oh
(74) Attorney, Agent, or Firm — Stinson Leonard Street LLP

(57) ABSTRACT

A process for epoxidizing an olefin comprising contacting an olefin with an oxidant in the presence of an insoluble oxidation catalyst in a solvent system comprising an organic water-miscible solvent to form an alkylene oxide. The insoluble oxidation catalyst comprises a metal, preferably selected from the group consisting of tungsten, cerium, and niobium. The metal is directly incorporated within a solid mesoporous silicate support, such as one selected from the group consisting of KIT-5, KIT-6, and TUD-1.

31 Claims, 19 Drawing Sheets

(56) References Cited

U.S. PATENT DOCUMENTS 6,525,208 B1 2/2003 Cheng et al.
2005/0197499 A1 9/2005 Shan et al.

OTHER PUBLICATIONS

Ramanathan, et al., "Direct Incorporation of Tungsten Into Ultra-Large-Pore Three Dimensional Mesoporous Silicate Framework: W-KIT-6", *Journal of Porous Materials*, vol. 12, No. 1, (2012) (10 pgs).

Ramanathan, et al., "Tungsten-Incorporated Cage-Type Mesoporous Silicate: W-KIT-5", *Microporous and Mesoporous Materials* 175 (2013) pp. 43-49 (7 pgs).

International Search Report and Written Opinion dated Dec. 16, 2013 issued for priority PCT/US2013/048077 filed on Jun. 27, 2013 (11 pgs).

Dedov, et al., "Catalytic Properties of Mesoporous Amorphous Silicates of Rare-Earth Elements in the Methane Oxidative Coupling Reaction", *Petroleum Chemistry*, vol. 50, No. 6 (2010) pp. 420-426 (7 pgs).

Van De Water, et al, "Ce-TUD-1: Synthesis, Characterization, and Testing of a Versatile Heterogeneous Oxidation Catayst", *Industrial & Engineering Chemistry Research*, vol. 26 (2007), pp. 4221-4225 (5 pgs).

Beck, et al., "A New Family of Mesoporous Molecular Sieves Prepared with Liquid Crystal Templates", *Journal of the American Chemical Society* 114(27) 10834-10843 (1992) (11 pgs).

Kim, et al., "Synthesis of MCM-48 Single Crystals", *Chemical Communications*, pp. 259-260 (1998) (2 pgs).

Strunk, et al., "Synthesis of Different $CeO_2$ Structures on Mesoporous Silica and Characterization of Their Reduction Properties", *Journal of Physical Chemistry C*, vol. 115, pp. 4114-4126 (2011) (13 pgs).

Yang, et al., "Size-Dependent Ramau Red Shifts of Semiconductor Nanocrystals", *Journal of Physical Chemistry B*, vol. 112, pp. 14193-14197 (2008) (5 pgs).

* cited by examiner

ALKYLENE EPOXIDATION WITH MESOPOROUS CATALYSTS

CROSS-REFERENCE TO RELATED APPLICATIONS

This application is based on and claims priority to U.S. Provisional Patent Application Ser. No. 61/690,476 and U.S. Provisional Patent Application Ser. No. 61/690,475, both filed on Jun. 27, 2012, which are both incorporated herein by reference in their entirety.

FIELD OF THE INVENTION

The present invention relates generally to the olefin epoxidation using supported metal catalysts in a liquid phase.

BACKGROUND OF THE INVENTION

Conventional epoxidation processes typically use silver-based catalysts for producing ethylene oxide (EO) from ethylene employing dioxygen as oxidant. The temperature and pressure for the conventional process are approximately 200° C. and 30 bars, respectively. Under these conditions, 10 to 15% of the ethylene in the conventional process is burned to carbon dioxide, rather than ethylene oxide, causing approximately $1 billion loss (based on global ethylene oxide production).

In the conventional process, the high temperatures employed result in the burning of the feedstock ethylene and product EO. To minimize this burning, a high ethylene gas hourly space velocity is maintained resulting in a per-pass ethylene conversion of 8%. At this low conversion, the selectivity towards EO is reported to be in the 85-90% range. Additional energy-intensive steps are required to separate and recycle the large amounts of unreacted ethylene from the product. Furthermore, the gaseous mixture of ethylene and EO is highly flammable in the presence of oxygen gas, which necessitates elaborate safety precautions in the design of the EO process equipment. Thus, there remains a need for an improved ethylene epoxidation process.

BRIEF SUMMARY OF THE INVENTION

The present invention is directed to a process for epoxidizing an olefin. The process generally comprises contacting an olefin with an oxidant in the presence of an insoluble oxidation catalyst in a solvent system comprising an organic water-miscible solvent to form an alkylene oxide. The insoluble oxidation catalyst comprises a metal, preferably selected from the group consisting of tungsten, cerium, and niobium. The metal is directly incorporated within a solid mesoporous silicate support, such as one selected from the group consisting of KIT-5, KIT-6, and TUD-1. There is no detectable carbon dioxide as a byproduct.

In a preferred aspect, the process involves contacting an olefin selected from the group consisting of ethylene and propylene with hydrogen peroxide in the presence of an insoluble oxidation catalyst in a solvent system comprising an organic water-miscible solvent to form ethylene oxide or propylene oxide. The insoluble oxidation catalyst comprises a metal selected from the group consisting of tungsten, cerium, and niobium which is directly incorporated within a solid mesoporous silicate support. There is no detectable carbon dioxide as a byproduct.

In another aspect, present invention is directed to a reaction mixture comprising an olefin, an oxidant, an insoluble oxidation catalyst, and a solvent system comprising an organic water-miscible solvent to form an alkylene oxide. The insoluble oxidation catalyst comprises a metal, preferably selected from the group consisting of tungsten, cerium, and niobium. The metal is directly incorporated within a solid mesoporous silicate support, such as one selected from the group consisting of KIT-5, KIT-6, and TUD-1.

One exemplary advantage of the present invention, especially in the context of EO production, is that the inventive epoxidation process is inherently safe. Because the inventive process uses a liquid oxidant (e.g., hydrogen peroxide), there is no oxygen present in the vapor phase of the reactor as long as hydrogen peroxide decomposition is avoided. Further, the ethylene oxide remains substantially dissolved in the liquid phase at the operating conditions. Thus, the formation of explosive mixtures with either ethylene or ethylene oxide in the vapor phase is avoided.

There are several attractive features that make the inventive process economically competitive with the conventional EO process. The near-quantitative selectivity to EO (>99%) and the elimination of burning conserve the valuable feedstock (ethylene) and reduce the carbon footprint associated with the production of this important chemical intermediate making this a clean technology. In addition, the low cost of the tungsten, cerium, and niobium metals (compared to silver) and easy recoverability and recyclability of heterogenized catalyst (e.g., W-KIT-6 and W-KIT-5) should make the inventive process cost competitive. Furthermore, the total avoidance of vapor phase flammability eliminates the need to maintain low per-pass ethylene conversions and for the addition of diluents such as argon, lowering the costs associated with the recycle of large amounts of unreacted ethylene and diluents. Commercialization of the process thus presents a tremendous opportunity for the EU industry to conserve oil and gas reserves due to the effective utilization of the feedstock.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION OF EXEMPLARY EMBODIMENT

Figure 1:
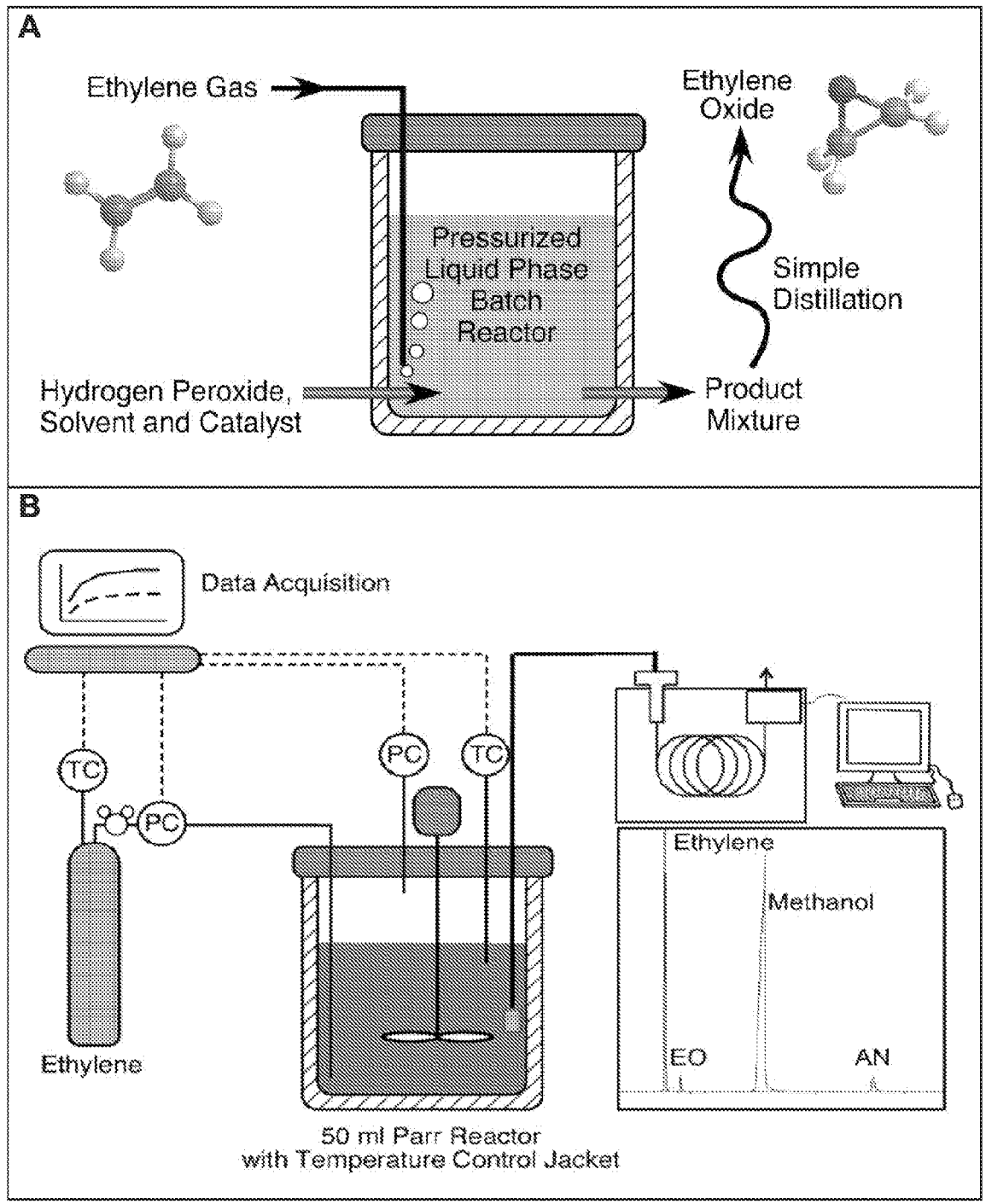
FIG. 1A is a schematic illustrating the epoxidation of ethylene in accordance with an exemplary embodiment of the present invention.
FIG. 1B shows the experimental setup and conditions utilized for an exemplary epoxidation reaction. In a typical reaction, the experimental conditions were as follows: methanol (solvent) 20 g; 50 wt % $H_2O_2/H_2O$ (oxidant)=8 g; acetonitrile (internal standard)=0.9 g; reactor pressure=50 bar; agitation speed=1400 rpm; temperature=35° C.; catalyst amount=300 to 500 mg; time=5 hours.

The present invention is directed to a process for the epoxidation of an olefin. The process generally comprises contacting the olefin and an oxidant with an insoluble oxidation catalyst in a solvent system comprising an organic water-miscible solvent to form a reaction system. The insoluble oxidation catalyst comprises a metal incorporated into a mesoporous silica support. Preferred metals include tungsten, cerium, and niobium. The process may be conducted in a batch or continuous reactor to produce the corresponding alkylene epoxide, preferably with no detectable carbon dioxide as byproduct. An overview of the process using ethylene epoxidation as an example is illustrated in FIG. 1A.

As shown herein, the epoxidation activities of the tungsten, cerium, and niobium incorporated catalysts are generally of the same order of magnitude as conventional silver catalysts (700 to 4,400 mg EO/h-gAg). The W-KIT-6 catalyst typically exhibits EO productivities of about 30 to 200 mg EO/h-gW. The W-KIT-5 catalyst typically exhibits EO productivities of about 10 to 120 mg EO/h-gW. The Ce-TUD-1 catalyst typically exhibits EO productivities of about 10 to 500 mg EO/h-gCe. The Nb-KIT-6 catalyst and Nb-KIT-5 catalyst typically exhibit EO productivities of about 200 to 1000 mg EO/h-gNb.

The present invention utilizes a metal catalyst incorporated in to a solid mesoporous silica support. The metal is preferably selected from the group consisting of tungsten, cerium, and niobium. According to the IUPAC definition, mesoporous materials are those having a pore size of about 2 nm to 50 nm (2, 4, 6, 8, 10, 12, 14, 16, 18, 20, 22, 24, 26, 28, 30, 32, 34, 36, 38, 40, 42, 44, 46, 48, or 50 nm). According to the IUPAC, a mesoporous material can be disordered or ordered in a mesostructure.

In one aspect, the mesoporous silicate material comprises the KIT series, such as KIT-1, KIT-5, and KIT-6. KIT-1 is described in U.S. Pat. No. 5,958,368, and other members of the KIT series are known (see, e.g., KIT-6 in Nanoscale Res Lett 4(11) 1303-1308 (2009)). KIT-5 and KIT-6 typically have a pore size of about 7 to 9 nm.

In another aspect, the mesoporous silicate material comprises the TUD series, such as TUD-1. TUD-1 is an amorphous mesoporous inorganic oxide having a unique pore structure with three-dimensionally randomly interconnected mesopores. The mesopores comprise at least about 97 volume percent of the pore volume based upon mesopores and micropores. Moreover, its mesopore size can be tuned from 1.5 nm to 30 nm to meet the requirements of various catalytic processes. TUD-1 has been shown to have a high surface area (e.g., 400 to 1100 $m^2$/g) and pore volume (0.4 to 2.0 $cm^3$/g), with the trade-off being pore size. Its X-ray diffraction pattern shows an intensive reflection peak between 0.5 and 3.0 degrees in 2θ, corresponding to a lattice d-spacing between 25 nm and 350 nm. TUD-1 material has been disclosed in U.S. Pat. No. 6,358,486, which is herein incorporated by reference.

In another aspect, the support comprises M41S series, including MCM-41 (hexagonal) and MCM-48 (cubic), and MCM-50. These materials have unique pore structures: MCM-41 possesses one-dimensional pores that are regularly arranged in parallel, whereas MCM-48 has three-dimensional, ordered pores. MCM-41 has a hexagonal crystal structure with a uni-dimensional pore system, while MCM-50 has a lamellar structure. The M41S materials and their synthesis are described in a number of Mobil patents, including U.S. Pat. Nos. 5,102,643, 5,057,296, 5,098,684, and 5,108,725, which are incorporated by reference, as well as in the literature in "The Discovery of ExxonMobil's M41S Family of Mesoporous Molecular Sieves", Kresge et al, *Studies in Surface Science and Catalysis,* 148 Ed. Terasaki, Elsevier bV (2004). The mean pore size is about 2 to 4 nm such that the use of the mesoporous materials is typically used in conjunction with lower olefins (e.g., ethylene and propylene).

In another aspect, the mesoporous silicate material comprises the SBA series, such as SBA-1, SBA-2, SBA-3, and SBA-15. Its channels are regularly arranged, while the constituent atoms show an arrangement similar to that of amorphous silica. U.S. Pat. No. 6,592,764 found a family of high quality mesoporous silicas, hydrothermal stability, and ultra-extensive pores size, through the synthesis with the use of an amphiphilic block copolymer in acid medium. A member of the family, SBA-15, has highly ordered mesostructure, hexagonal in two dimensions (p6mm) similar to a honeycomb. Other structures as cubic in cage form, or three-dimensional hexagonal are also formed. SBA-1, SBA-2, and SBA-3 were described in Huo et al., *Mesostructure Design with Gemini Surfactants: Supercage Formation in a Three-Dimensional Hexagonal Array*, Science 268 1324-1327 (1995). SBA-15 is described in Zhao, et al., *Triblock Copolymer Syntheses of Mesoporous Silica with Periodic 50 to 300 Angstrom Pores*, Dongyuan Science 279 (279) (1998).

In one exemplary embodiment, the catalyst comprises a metal, such as tungsten, and the mesoporous silicate, such as KIT-6. The catalyst may have a specific surface area ($S_{BET}$) of about 500 to 1500 m$^2$/g (e.g., about 500, 600, 700, 800, 900, 1000, 1100, 1200, 1300, 1400, 1500 m$^2$/g, or some range therebetween). The catalyst may have a pore volume ($V_p$) of about 0.8 to 1.8 cc/g (e.g., about 0.8, 0.9, 1.0, 1.1, 1.2, 1.3, 1.4, 1.5, 1.6, 1.7, 1.8 cc/g, or some range therebetween). The catalyst may have an average pore diameter ($d_P$) of about 2 to 10 nm (e.g., about 2, 3, 4, 5, 6, 7, 8, 9, 10 nm, or some range therebetween).

In another exemplary embodiment, the catalyst comprises a metal, such as cerium, and the mesoporous silicate, such as TUD-1. The catalyst may have a specific surface area ($S_{BET}$) of about 100 to 1000 m$^2$/g (e.g., about 100, 200, 300, 400, 500, 600, 700, 800, 900, 1000 m$^2$/g, or some range therebetween). The catalyst may have a pore volume ($V_p$) of about 0.5 to 1.5 cc/g (e.g., about 0.5, 0.6, 0.7, 0.8, 0.9, 1.0, 1.1, 1.2, 1.3, 1.4, 1.5 cc/g, or some range therebetween). The catalyst may have an average pore diameter ($d_P$) of about 2 to 20 nm (e.g., about 2, 3, 4, 5, 6, 7, 8, 9, 10, 11, 12, 13, 14, 15, 16, 17, 18, 19, 20 nm, or some range therebetween).

In another exemplary embodiment, the catalyst comprises a metal, such as niobium and the mesoporous silicate, such as KIT-5 or KIT-6. The catalyst may have a specific surface area ($S_{BET}$) of about 500 to 1500 m$^2$/g (e.g., about 500, 600, 700, 800, 900, 1000, 1100, 1200, 1300, 1400, 1500 m$^2$/g, or some range therebetween). The catalyst may have a pore volume ($V_p$) of about 0.5 to 1.8 cc/g (e.g., about 0.5, 0.6, 0.7, 0.8, 0.9, 1.0, 1.1, 1.2, 1.3, 1.4, 1.5, 1.6, 1.7, 1.8 cc/g, or some range therebetween). The catalyst may have an average pore diameter ($d_P$) of about 5 to 15 nm (e.g., about 5, 6, 7, 8, 9, 10, 11, 12, 13, 14, 15 nm, or some range therebetween). Pore diameters of about 7 to 9 nm are typical.

Preferred metals incorporated into the mesoporous silicate include tungsten, cerium, and niobium. In one aspect, the tungsten is in the form of lithium tungstate, sodium tungstate, potassium tungstate, cesium tungstate, magnesium tungstate, calcium tungstate, barium tungstate, ammonium tungstate, cadmium tungstate, cerium tungstate, cobalt tungstate, copper tungstate, silver tungstate, or combinations thereof. In another aspect, the cerium is in the form of cerium nitrate, cerium sulphate, cerium acetate, cerium chloride, ceric ammonium nitrate, and combinations thereof. In another aspect, the niobium is in the form of niobium chloride, niobium oxychloride, niobium fluoride, niobium bromide, and niobium oxalate.

The catalyst typically has a metal to mesoporous silicate molar ratio of about 5 to 150 (e.g., about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, or some range therebetween). For example, the Si/W, Si/Ce, or Si/Nb molar ratio is within this range.

The catalyst typically has a unit cell parameter ($a_0 = d_{211}/\sqrt{(h^2+k^2+l^2)}$) of about 15 to 30 nm (e.g., about 15, 16, 17, 18, 19, 20, 21, 22, 23, 24, 25, 26, 27, 28, 29, 30 nm, or some range therebetween). Typically, the unit cell parameter is about 19 to 25 nm.

Various oxidants can be used for the epoxidation of alkenes, such as molecular oxygen, hydrogen peroxide, organic hydroperoxide (e.g., tert-butyl hydroperoxide) and organic peracids (e.g., peroxyformic acid). It is preferably to use hydrogen peroxide or tert-butyl hydroperoxide.

In conducting the epoxidation, hydrogen peroxide may be used neat or as an aqueous solution. The concentration of hydrogen peroxide in the aqueous solution can be in the range of about 5 to about 80 wt % (e.g., about 5, 10, 15, 20, 25, 30, 35, 40, 45, 50, 55, 60, 65, 70, 75, or 80 wt %), but is preferably in the range of about 30 wt % to about 70 wt % (e.g., about 30, 35, 40, 45, 50, 55, 60, 65, or 70 wt %), and more preferably in the range about 45 wt % to about 55 wt %.

The catalysts result in significant hydrogen peroxide decomposition. Further, as demonstrated herein, the W-KIT-6 and Ce-TUD-1 have nearly complete selectivity towards EO with no $CO_2$ and the other byproducts being formed. Nb-KIT-6 has no $CO_2$ being formed but contains some other byproduct.

In one aspect, the organic water miscible solvent is selected from the group consisting of a $C_1$ to $C_4$ alcohol, such as methanol, ethanol, propanol isopropanol, butanol, tert-butanol, and the like. Other exemplary solvents are those set forth in U.S. Pat. Nos. 5,939,568 and 6,271,400, and include tetrahydrofuran, acetonitrile, and aromatic hydrocarbons such as toluene and xylene. Of these, methanol is preferred.

In one aspect, the solvent system further comprises water. The ratio of the organic water miscible solvent to water weight ratio ranges from about 3:1 to 24:1 (e.g., about 3:1, 6:1, 9:1, 12:1, 15:1, 18:1, 21:1, or 24:1), with weight ratios of 13:1 to 22:1 being preferred. It will be appreciated that water may be present in the initial reaction mixture (e.g., from aqueous hydrogen peroxide) and will also be produced as a byproduct of the epoxidation reactions.

The epoxidizing process preferably occurs at a temperature of less than about 50° C. (e.g., less than about 50, 45, 40, 35, 30, 25° C., or some range therebetween). In one aspect, the epoxidizing process occurs at temperature of about the 20 to 40° C.

The reaction time for the epoxidation process is typically about 0.5 to 20 hours (e.g., about 0.5, 1, 2, 3, 4, 5, 6, 7, 8, 9, 10, 11, 12, 13, 14, 15, 16, 18, 18, 19, 20 hours, or some range therebetween). In one aspect, the reaction time is about 2 to 8 hours, preferably about 3 to 7 hours, and more preferably about 4 to 6 hours.

The epoxidizing process preferably occurs at a pressure of less than 70 bar (e.g., less than about 70, 65, 60, 55, 50, 45, 40, 35, 30, 25, 20 bar, or some range therebetween). In one aspect, the epoxidizing process occurs at a pressure of about 40 to 60 bar.

In one exemplary aspect, the present invention involves a tungsten-based catalyst for the production of alkylene oxide, preferably ethylene oxide or propylene oxide, from the corresponding alkylene, preferably ethylene or propylene. The epoxidation process uses a tungsten catalyst incorporated into an ordered mesoporous silicate material (e.g., KIT-6, KIT-5).

The process is operated in a reactor in which the solid catalyst particles are suspended in a liquid phase containing the liquid oxidant (e.g., hydrogen peroxide) dissolved in a solvent system (e.g., methanol mixture). The reactor is preferably operated at mild temperatures (e.g., about 20-40° C.) and the ethylene is admitted at relatively low pressures (e.g., about 40 to 60 bars) to exclusively make EO or PO with no detectable carbon dioxide as a byproduct.

In one aspect, the tungsten catalysts of the present invention are heterogeneous and insoluble. The tungsten used in this invention is heterogenized by incorporating the active metal heteroatom into the inert framework of the cubic mesoporous silicates (e.g., KIT-6 and KIT-5). This novel heterogenized tungsten catalyst selectively epoxidizes olefin to its corresponding epoxide (e.g., ethylene to EO or propylene to PO).

In another exemplary aspect, the present invention involves a cerium-based catalyst for the production of alkylene oxide, preferably ethylene oxide or propylene oxide, from the corresponding alkylene, preferably ethylene or propylene. The epoxidation process uses a cerium catalyst incorporated into an amorphous mesoporous silicate material (e.g., TUD-1). The process is operated in a reactor in which the solid catalyst particles are suspended in a liquid phase containing the liquid oxidant (e.g., hydrogen peroxide) dissolved in a solvent system (e.g., methanol mixture). The reactor is preferably operated at mild temperatures (e.g., about 20-40° C.) and the ethylene or propylene is admitted at relatively low pressures (e.g., about 40 to 60 bars) to exclusively make EO or PO with no detectable carbon dioxide as a byproduct.

In one aspect, the cerium catalysts of the present invention are heterogeneous and insoluble. The cerium used in this invention is heterogenized by incorporating the active metal heteroatom into the inert framework of the amorphous mesoporous silicates (e.g., TUD-1). This novel heterogenized cerium catalyst selectively epoxidizes olefin to its corresponding epoxide (e.g., ethylene to EO or propylene to PO).

In yet another exemplary aspect, the present invention involves a niobium-based catalyst for the production of alkylene oxide, preferably ethylene oxide or propylene oxide, from the corresponding alkylene, preferably ethylene or propylene. The epoxidation process uses a niobium catalyst incorporated into an ordered mesoporous silicate material (e.g., KIT-6, KIT-5). The process is operated in a reactor in which the solid catalyst particles are suspended in a liquid phase containing the liquid oxidant (e.g., hydrogen peroxide) dissolved in a solvent system (e.g., methanol mixture). The reactor is preferably operated at mild temperatures (e.g., about 20-40° C.) and the ethylene or propylene is admitted at relatively low pressures (e.g., about 40 to 60 bars) to exclusively make EO or PO with no detectable carbon dioxide as a byproduct.

In one aspect, the niobium catalysts of the present invention are heterogeneous and insoluble. The niobium used in this invention is heterogenized by incorporating the active metal heteroatom into the inert framework of the cubic mesoporous silicates (e.g., KIT-6 and KIT-5). This novel heterogenized niobium catalyst selectively epoxidizes olefin to its corresponding epoxide (e.g., ethylene to EO or propylene to PO).

Various epoxidizable olefinic compounds can be epoxidized in the practice of this invention. In a preferred aspect, the olefin is ethylene or propylene. Other olefins that may possibly be selectively epoxidized using this heterogenized catalyst include butenes, butadiene, pentenes, isoprene, 1-hexene, 3-hexene, 1-heptene, 1-octene, diisobutylene, 1-nonene, their double-bond positional isomers, and mixtures thereof. In another aspect, the alkenes may be selected from the group consisting of 1-propene, 2-methyl-1-propene, 1-butene, 1-pentene, 4-methyl-1-pentene, 1-hexene, 3-ethyl-1-hexene, 4-n-propyl-1-heptene, 1-octene, 1-nonene, 1-undecene, 1-dodecene, 5-methyl-1-dodecene, 1-tetradecene, 1-hexadecene, and the like.

The processes of this invention may be performed in a batch mode, semi-batch mode, or continuous mode.

The following examples set forth exemplary techniques for carrying out the synthesis of the catalysts and their use in epoxidation reactions. It is to be understood, however, that these examples are provided by way of illustration only, and nothing therein should be considered as a limitation upon the overall scope of the invention.

Example 1A

Synthesis of W-KIT-6

Figure 2:
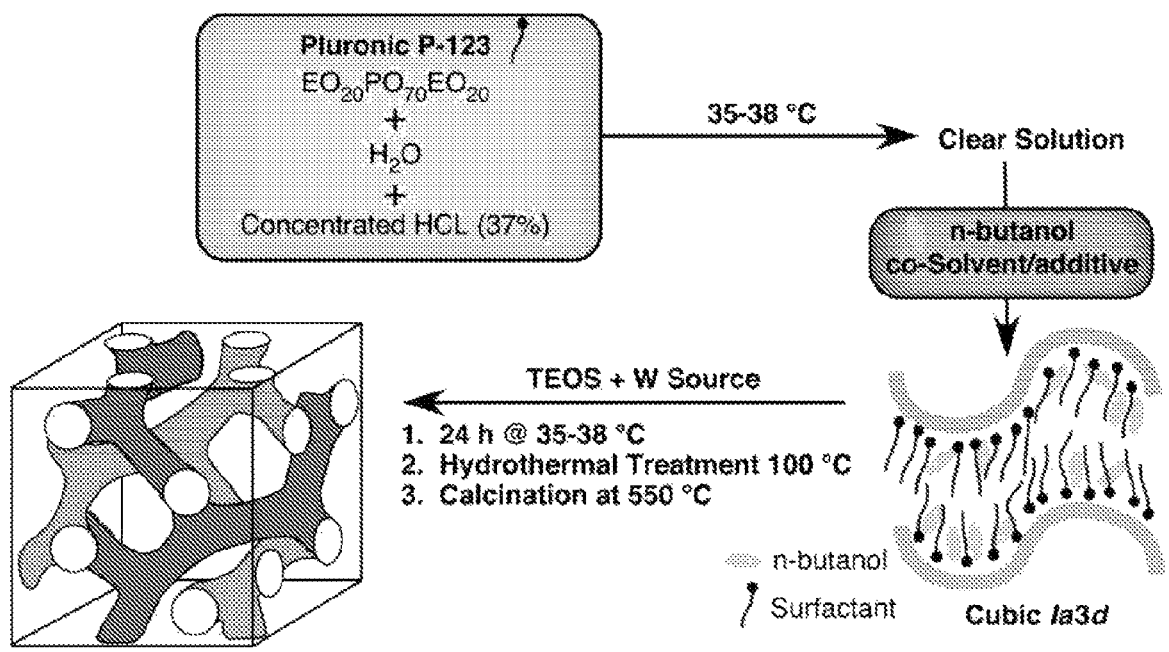
FIG. 2 is a scheme outlining the synthesis of W-KIT-6.

Mesoporous W-KIT-6 materials were synthesized following the procedure reported for synthesizing high quality siliceous KIT-6 material in Kim et al., *MCM-48-like large mesoporous silicas with tailored pore structure: facile synthesis domain in a ternary triblock copolymer-butanol-water system*, Am Chem Soc 127 7601-7610 (2005). The W-incorporated materials are denoted as W-KIT-6 (molar Si/W value). In a typical synthesis, 5.0 g of triblock copolymer Pluronic P123 ($EO_{20}$-$PO_{70}$-$EO_{20}$, Aldrich) was dissolved in 185 mL of 0.5 M HCl solution at 35° C. Then 5.0 g of n-butanol (Aldrich) were added and the stirring continued for another 60 minutes. Then 10.6 g of tetraethyl orthosilicate (TEOS, Aldrich) and required amounts of sodium tungstate (Acros Organics) were added. The resulting reaction mixture was stirred at 35° C. for 18 hours and then hydrothermally treated at 98° C. for 48 hours under static conditions in a Teflon-lined stainless steel autoclave. The solid product was filtered without washing, dried at 100° C. overnight, and calcined in a flow of air at 550° C. for 5 hours. An overview of the synthesis of W-KIT-6 is illustrated in FIG. 2.

Example 1B

Synthesis of W-KIT-5

The synthesis of W-KIT-5 materials was carried out following the procedure reported for synthesizing high quality siliceous KIT-5 material (see Kleitz et al., *Large Cage Face-Centered-Cubic Fm3m Mesoporous Silica: Synthesis and Structure*, J. Phys. Chem. B 107 14296-14300 (2003)). In a typical synthesis, 3.6 g of triblock copolymer Pluronic F127 (Sigma) were dissolved in 180 ml of 0.4 M HCl solution at 45° C. Then 16.9 g of tetraethyl orthosilicate (TEOS 98%, Aldrich) and required amounts of sodium tungstate (Acros Organics) were added. The resulting reaction mixture was stirred at 45° C. for 18 h and then hydrothermally treated at 98° C. for 24 h under static conditions in a Teflon-lined stainless steel autoclave. The solid product was filtered without washing, dried at 100° C. overnight and calcined in a flow of air at 550° C. for 5 hours. The resulting solids are denoted as W-KIT-5 (molar Si/W ratio).

Example 2

Characterization of W-KIT-6

2-D SAXS patterns were collected on a Rigaku system with an S-MAX 3,000 instrument using a Bede Scientific microfocus tube source operating at 45 kV and 0.66 mA. Patterns were rotationally averaged and presented as intensity versus scattering angle. A 10×10 cm wire detector was placed approximately 150 cm from the sample position and silver behenate was used to determine the exact pixel to scattering angle conversion. Room temperature x-ray powder patterns in the high angle were obtained using monochromated CuKa radiation ($\lambda$=1.54178 Å) on a Bruker Proteum Diffraction System equipped with Helios multilayer optics, an APEX II CCD detector and a Bruker MicroStar microfocus rotating anode x-ray source operating at 45 kV and 60 mA. The powder samples were mixed with a small amount of Paratone N oil to form a paste that was then placed in a small (less than 0.5 mm) nylon kryoloop and mounted on a goniometer head. The specimen was then positioned at the goniometer center-of-motion by translating it on the goniometer head. Three overlapping 1 minute 1808 φ-scans were collected using the Bruker Apex2 V2010.3-0 software package with the detector at 2θ=30°, 60°, and 90° using a sample-to-detector distance of 50.0 mm. These overlapping scans were merged and converted to a .RAW file using the Pilot/XRD2 evaluation option that is part of the APEX2 software package. This .RAW file was then processed using the Bruker EVA powder diffraction software package.

The textural properties (surface area, pore volume, and pore size distribution) were evaluated from nitrogen sorption isotherms at −196° C. Prior to the physisorption experiment, the samples were dried in vacuum at 200° C. for 16 hours, and the nitrogen adsorption and desorption isotherms were obtained with a Quantachrome Autosorb-6B instrument. The Brunauer-Emmett-Teller (BET) equation was used to calculate the apparent surface area from adsorption data obtained at $P/P_0$ between 0.05 and 0.3. The total pore volume was calculated from the amount of nitrogen adsorbed at $P/P_0$=0.98 and the pore size distribution was calculated by analyzing the adsorption branch of the $N_2$ sorption isotherm using the Barret-Joyner-Halenda (BJH) method. Elemental analysis was carried out by using instrumental neutron activation analysis (INAA) on the Hoger Onderwijs Reactor, which is a nuclear reactor at the Technische Universiteit Delft with a thermal power of 2 MW and maximum neutron reflux of $2.10\,m^{-2}\,s^{-1}$. The following steps were involved: samples were irradiated with neutrons in the nuclear reactor followed by a period of decay during which the resulting radioactivity due to irradiation was measured. The energy of the radiation and the half-life period of the radioactivity enable a highly accurate quantitative analysis.

Scanning Transmission Electron Microscopy Images (STEM Images)

STEM Images were captured using an FEI High Angle Annular Dark-Field Detector (HAADF) and Transmission Electron Micrographs were captured using a 2 K×2 K CCD, each mounted on a 200 kV FEI Technai F20 G2 X-Twin Field Emission Scanning/Transmission Electron Microscope operating at 200 kV. Samples were dispersed in ethanol, and a drop of the suspension was placed on Lacey Carbon supported on 300 mesh copper grids. Raman spectra of W-KIT-6 powder samples were acquired on a SENTERRA (Bruker) dispersive Raman microscope equipped with a thermoelectrically cooled CCD detector and an Argon laser. Diffuse reflectance UV-Vis spectra were collected in the 200-700 nm range at room temperature, using $BaSO_4$ as the reference, with a Thermoscientific (Evolution 600) spectrophotometer equipped with a diffuse reflectance accessory.

X-Ray Photoelectron Spectroscopy

X-ray photoelectron spectroscopy data were recorded on a Physical Electronics PHI 5800 ESCA system with standard non-monochromatic Al X-rays (1486.6 eV) operated at 250 W and 15 kV in a chamber pumped down to a pressure of approximately $1.0\times10^{-8}$ Torr. A 93.9 eV and 58.7 eV pass energy were typically used for survey and specific element analysis, respectively. The electron takeoff angle was 45° with respect to the sample surface. The binding energies were corrected with reference to carbon at 284.8 eV. The curve fitting was done using XPSPEAK with constrains applied to peak position, area as well as FWHM (full width at half maximum).

Temperature Programmed Reduction ($H_2$-TPR) and Temperature Programmed Desorption of Ammonia ($NH_3$-TPD)

Temperature programmed Reduction ($H_2$-TPR) and Temperature programmed desorption of ammonia ($NH_3$-TPD) was carried out with a Micromeritics Autochem 2910 instrument equipped with a Thermal Conductivity Detector (TCD). For $H_2$-TPR, about 100 mg of W-KIT-6 sample is loaded in the sample tube and heated to 600° C. in a flow of helium and subsequently cooled to ambient temperature. Then $H_2$/Ar mixture is flown through the tube and the temperature was raised to 1050° C. at a ramp of 10° C./min and the consumption of hydrogen was monitored using TCD detector.

For $NH_3$-TPD, about 100 mg of W-KIT-6 samples were heated from room temperature to 250° C. to remove adsorbed water and were cooled down immediately to 100° C. in a flow of helium (10 sccm). Ammonia was adsorbed at this temperature for 30 minutes from a He stream containing 9.98 vol % $NH_3$ flowing at 10 sccm. Then the gas flow was switched to helium (10 sccm) and continued for another 30 minutes in order to remove any physisorbed ammonia. Following this step, the temperature was raised from 100° C. to 550° C. at a ramp of 10° C./min and the desorbed ammonia was recorded.

Structural Characterization

Figure 3:
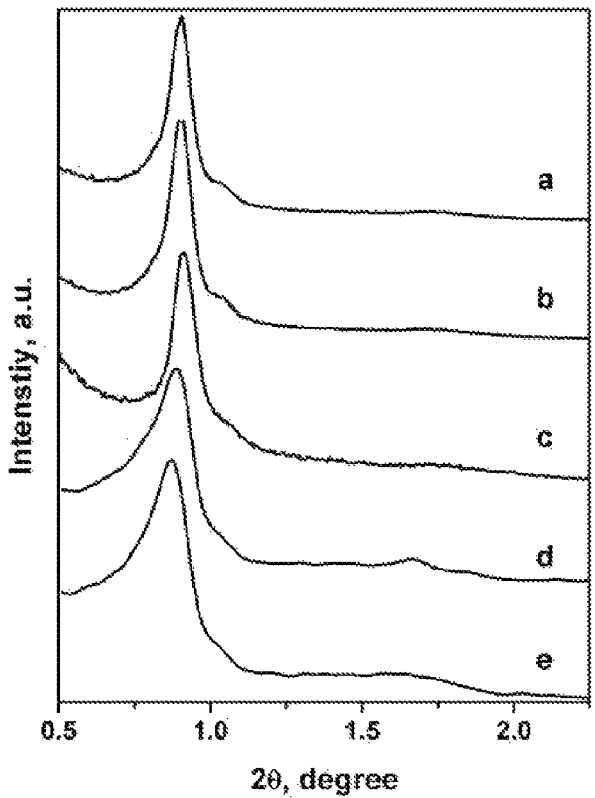
FIG. 3 shows the small angle XRD powder patterns of calcined W-KIT-6 samples with a molar Si/W ratio of (a) 100, (b) 70, (c) 40, (d) 20, and (e) 10.

Low angle powder XRD (0.5°-5°) pattern of different tungsten substituted KIT-6 samples are shown in FIG. 3. All the samples exhibit reflections similar to that of cubic Ia3d symmetry. An intense peak observed between 0.85° and 0.95°, which decreases with increase in tungsten content, is attributed to the 211 plane and represents high quality and structural order of these materials. The cubic unit cell parameter ($a_0$) and $d_{211}$ spacing values for all the materials are presented in Table 1. Marginal increase in a value was observed with an increase in tungsten content, especially at higher loadings. The ionic radius of tungsten is higher than that of silica and the incorporation of tungsten leads to marginal increase in unit cell parameter. As seen in FIG. 3, the $d_{211}$ peak characteristics change moderately with an increase in tungsten loading which is attributed to not only increased incorporation of tungsten in the framework but also the presence of extraframework tungsten species, especially at higher loadings.

Textural Characterization

Figure 4:
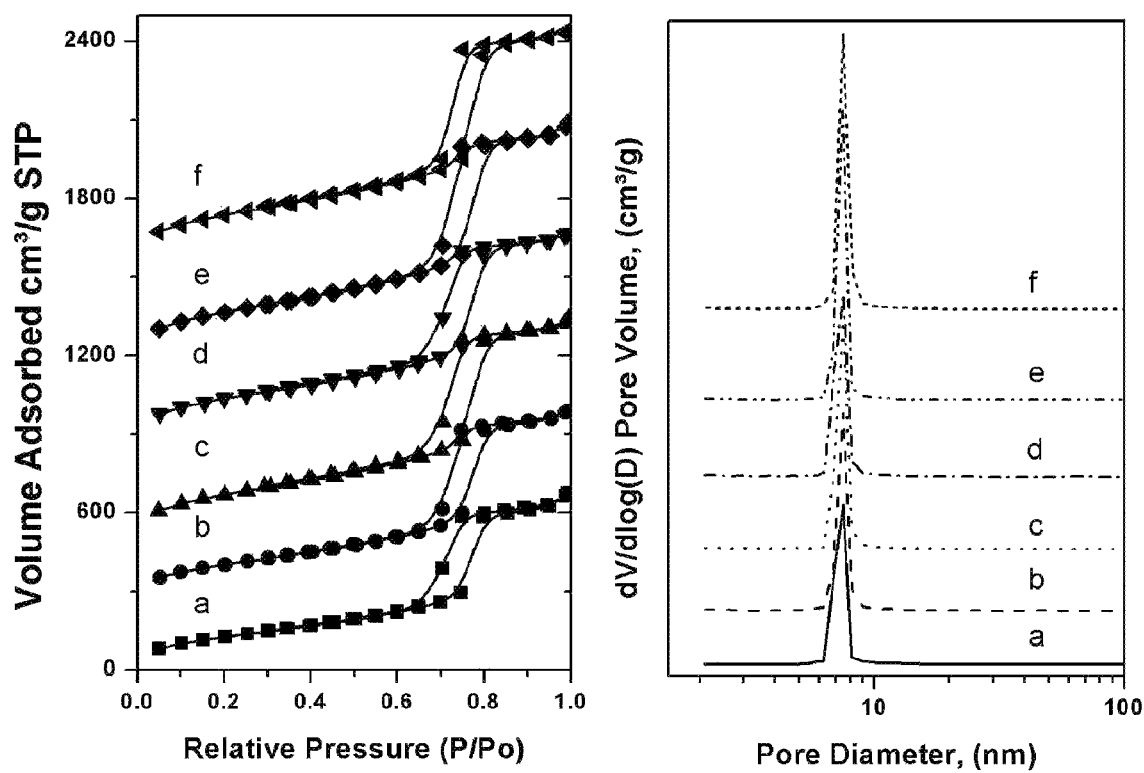
FIG. 4 shows the $N_2$ sorption isotherms (left panel) and adsorption pore size distributions (right panel) for W-KIT-6 samples synthesized with molar Si/W ratios of (a) 100, (b) 70, (c) 40, (d) 20, (e) 10, and (f) No W.

Nitrogen sorption isotherms and the corresponding pore size distribution for W-KIT-6 samples with different molar Si/W ratios compared with Si-KIT-6 are presented in FIG. 4. The BET surface area, pore volume and pore diameter obtained from the $N_2$ sorption studies for the various W-KIT-6 samples are listed in Table 1. All W-KIT-6 samples exhibited Type IV isotherm with H1 hysteresis loop typical of mesoporous solids with narrow pore size distribution. A sharp inflection in pore volume curve was observed at a relative pressure between 0.7 and 0.8 indicating capillary condensation within the uniform mesopores typical for KIT-6 materials. The BET surface area decreased from 927 $m^2$/g (for Si/W=100) to 625 $m^2$/g (for Si/W=10) and the pore volume decreased from 1.44 to 1.09 cm³/g respectively. The pore size distribution remained narrow between 6.3 nm and 6.9 nm for all W loadings.

Electron Microscopy Characterizations

Figure 5:
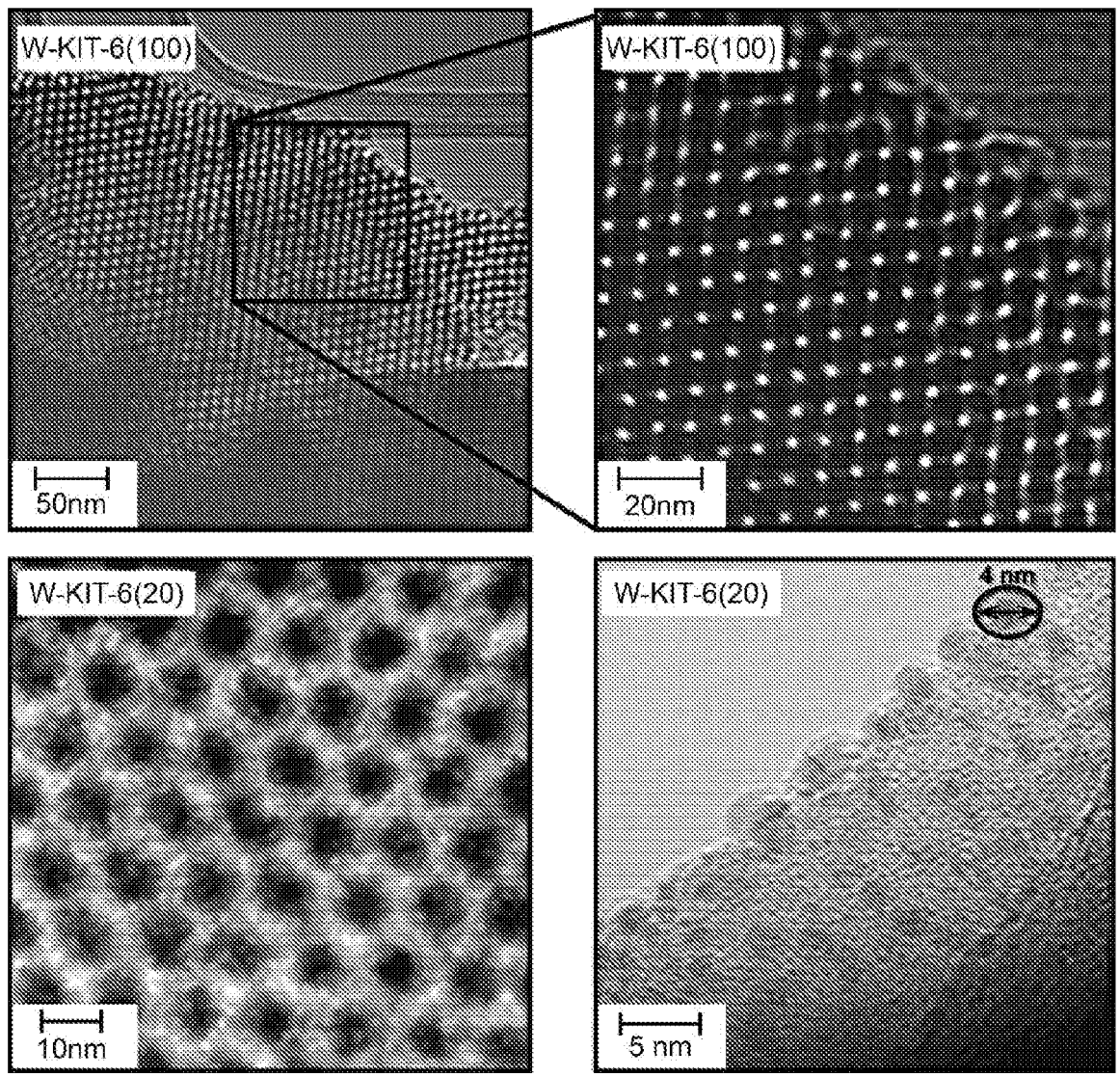
FIG. 5 contains representative Transmission Electron Micrographs (TEM) of W-KIT-6.

Representative TEM bright field images of W-KIT-6 (100 and 20) are shown in FIGS. 5 (*a, b,* and *d*). Highly ordered mesopore structures of W-KIT-6 materials are evident from these images and are in line with nitrogen sorption studies. In order to understand the dispersion of tungsten species, TEM dark field analysis was performed for W-KIT-6 (20) and the corresponding images are shown in FIG. 5(*c*). The white contrasting points are due to tungsten which showed a homogeneous dispersion. The presence of tungsten oxide nanoparticles is visible at higher magnification and the size is estimated to be 2-4 nm. Average pore size estimated from intensity profiles across TEM micrographs is around 6-7 nm and the average thickness of the wall is estimated to be 2-4 nm. The estimated pore diameter is in agreement with the results of the $N_2$ adsorption study.

Characterization of W Species

Figure 6:
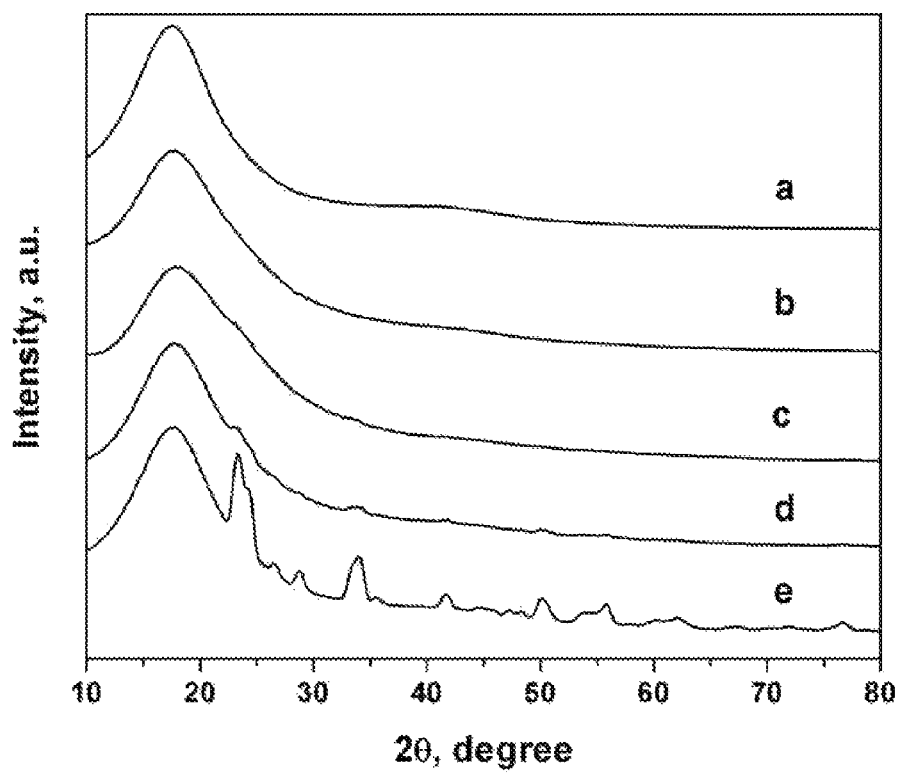
FIG. 6 shows the wide angle XRD powder patterns of calcined W-KIT-6 samples with a molar Si/W ratio of (a) 100, (b) 70, (c) 40, (d) 20, and (e) 10.

High angle (5°-80°) XRD patterns of the W-KIT-6 are depicted in FIG. 6. No characteristic reflections of $WO_3$ were observed in W-KIT-6 samples with Si/W ratio of 100 and 70. However, at increased tungsten contents, diffraction peaks corresponding to bulk $WO_3$ were detected and their intensities increase with the amount of tungsten. Zhang et al., *Synthesis, characterization, and catalytic testing of W-MCM-41 mesoporous molecular sieves*, Appl Catal A Gen 179 11-19 (1999), reported that tungsten can be incorporated into the MCM-41 framework without forming crystalline $WO_3$ for W loadings up to 5.6 wt %. Dai et al., *Novel economic and green approach to the synthesis of highly active W-MCM41 catalyst in oxidative cleavage of cyclopentene*, Chem Commun 7 892-893 (2003), doped tungsten into MCM-41 and reported a critical Si/W value of 30 beyond which the formation of extraframework $WO_3$ occurs. In contrast, no crystalline $WO_3$ was observed for tungsten incorporated MCM-48 sample (Si/W=45) prepared by rapid and facile room-temperature procedure. Similarly, no extraframework $WO_3$ species were found in W-MCM-41 (Si/W=31) prepared in the presence of $H_2O_2$ in acid medium as compared to a sample prepared without $H_2O_2$. However, Raman peaks due to $WO_3$ were observed in high W content MCM-41 sample (Si/W=19). Under highly acidic synthesis conditions (0.5 HCl), formation extraframework $WO_3$ species could not be avoided when Si/W is 40 or lower. Elemental analysis measured by instrumental neutron activation analysis (INAA) revealed that most of the tungsten in the synthesis gel was retained within the KIT-6 silica matrix.

Figure 7:
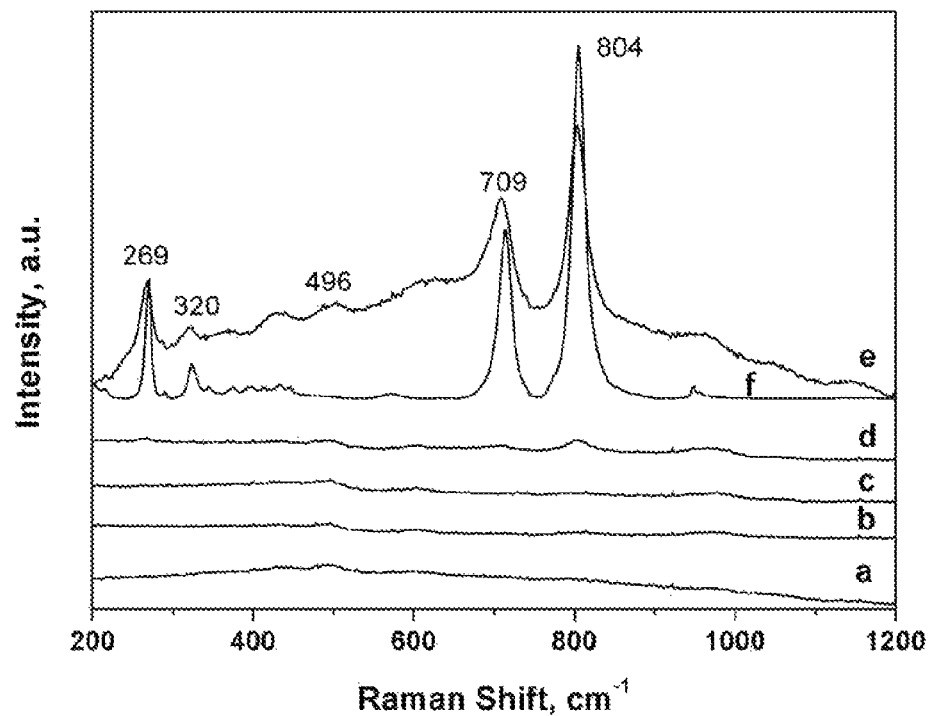
FIG. 7 is the Laser Raman spectra of calcined W-KIT-6 samples with a molar Si/W ratio of (a) infinity, (b) 100, (c) 70, (d) 40, (e) 20, and (f) 10.

The nature of the tungsten species in the KIT-6 material was also investigated using Laser Raman spectroscopy. Raman spectra of W-KIT-6 samples compared with Si-KIT-6 are shown in FIG. 7. For Si-KIT-6 and W-KIT-6 (Si/W=100 and 70) only a peak originating from amorphous silica (about 495 cm$^{-1}$) could be observed. For all other W-KIT-6 samples (Si/W=10, 20, and 40). Raman bands are observed at 804, 709, 323, and 269 cm$^{-1}$ and is characteristic of octahedral crystalline $WO_3$. The intensity of these bands increases with tungsten content. These results are in line with high angle XRD observations.

Figure 8:
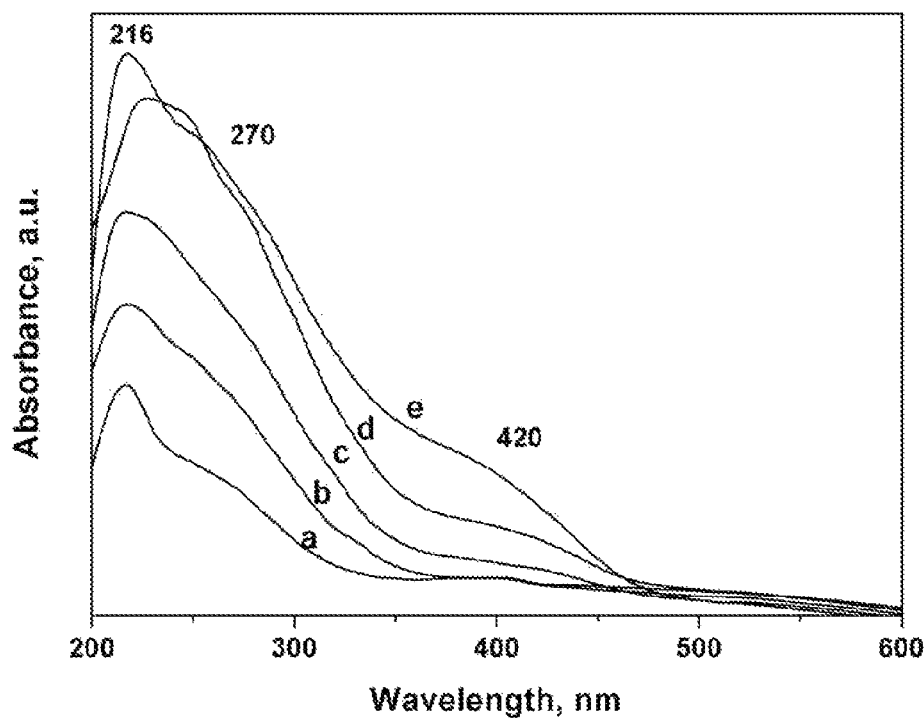
FIG. 8 shows the diffuse reflectance UV-Vis spectra of calcined W-KIT-6 samples with a molar Si/W ratio of (a) 100, (b) 70, (c) 40, (d) 20, and (e) 10.

Diffuse reflectance UV-Vis (DR-UV-Vis) spectroscopy is a sensitive tool for detection of framework incorporated metal and extra framework metal oxide in different mesostructures. The DR-UV-Vis spectra of all W-KIT-6 samples (FIG. 8) show an intense band centered around 216 nm. This is attributed to ligand to-metal charge transfer in isolated $[WO_4]$ tetrahedral species and is a direct proof for the framework incorporation of tungsten species in silica framework. The presence of shoulders around 270 nm may be attributed to $O^{2-} \rightarrow W^{6+}$ charge transfer, indicating the existence of partially polymerized W species in octahedral coordination. As the nuclearity of tungsten entities decreases, a blue shift of absorption from 350 nm to 240 nm had been observed previously for tungsten containing mesoporous silicas. Even at lower tungsten loadings, low nuclearity tungsten oxide species coexist with framework incorporated tungsten. The reported absorption band edge of bulk $WO_3$ is about 420 nm. The presence of this band in the DR-UV-Vis spectra of W-KIT-6 (20 and 10) samples thus confirms the existence of bulk $WO_3$ species apart from framework incorporated tungsten species. These results are also consistent with the results observed with high angle XRD (see FIGS. 3, 6, and discussion thereof).

Figure 9:
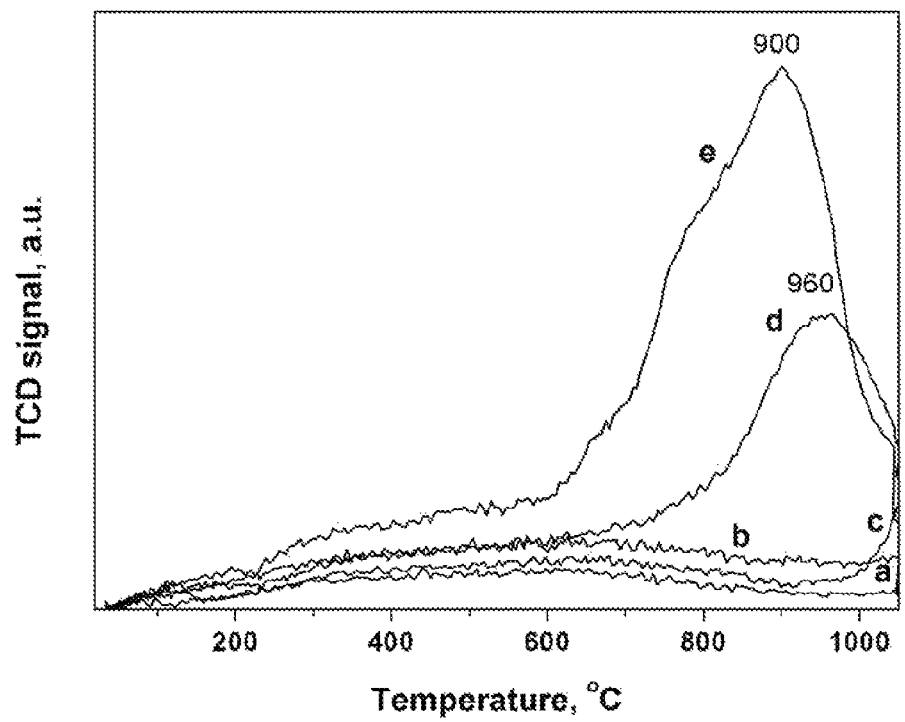
FIG. 9 shows the $H_2$-TPR profile of W-KIT-6 samples with a molar Si/W ratio of (a) 100, (b) 70, (c) 40, (d) 20, and (e) 10.

The $H_2$-TPR results (FIG. 9) provide relative estimations of reducible tungsten species on the various W-KIT-6 samples normalized based on the amount of the samples. As seen in FIG. 9, the W-KIT-6 (Si/W=100 and 70) samples did not show any reduction peak in the investigated temperature range (ambient to 1050° C.). However, a growing peak was observed at very high temperature 1050° C. for W-KIT-6 (40). On the other hand, prominent reduction peak with maxima at 960° C. and 900° C. were observed for W-KIT-6 (20) and W-KIT-6 (10) respectively. A shoulder around 750° C. was also noted for W-KIT-6 (10) which can be assigned to reduction of bulk supported $WO_3$ crystallites. The high temperature reduction peaks may be due to reduction of $W^{6+}$ species in tetrahedral coordination. The shift of reduction of peaks to high temperature with decrease in tungsten content suggests strong interaction of highly dispersion of tungsten species in tetrahedral coordination.

Figure 10:
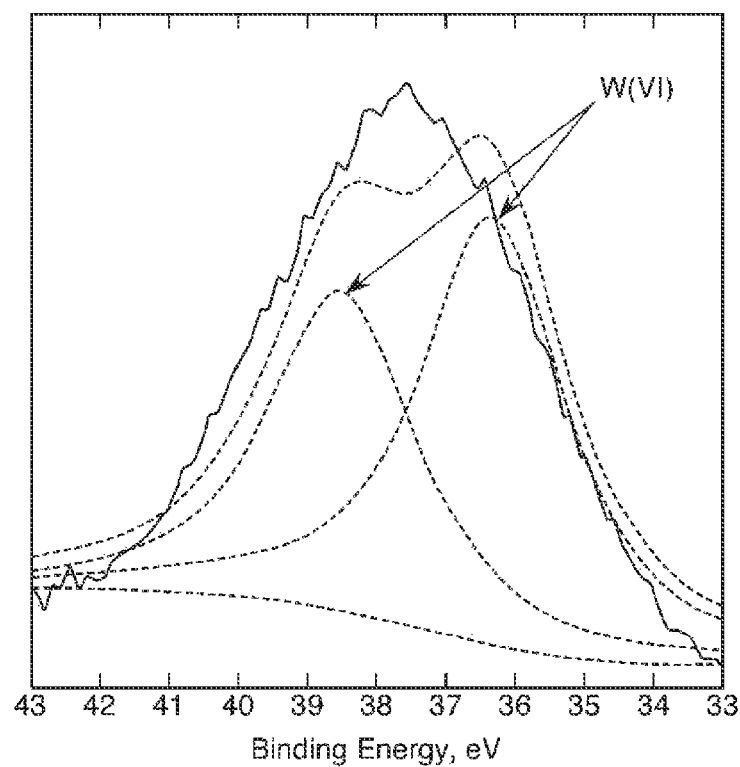
FIG. 10 shows the XPS spectra of W-KIT-6(20) (solid line—original XPS spectrum, dotted lines—XPSPEAK curve fitting).

FIG. 10 shows the $W_{4f}$ XPS spectra of W-KIT-6 (20) sample. Two peaks could be resolved and the observed $W_{4f}$ spectral lines at 38.5 and 36.3 eV can be assigned to presence of tungsten in 6+ oxidation state. Hence, apart from presence of extraframework $WO_3$, the suggested interaction of tungsten to silica is shown below.

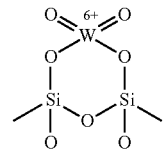

Acidity Characterization

Figure 11:
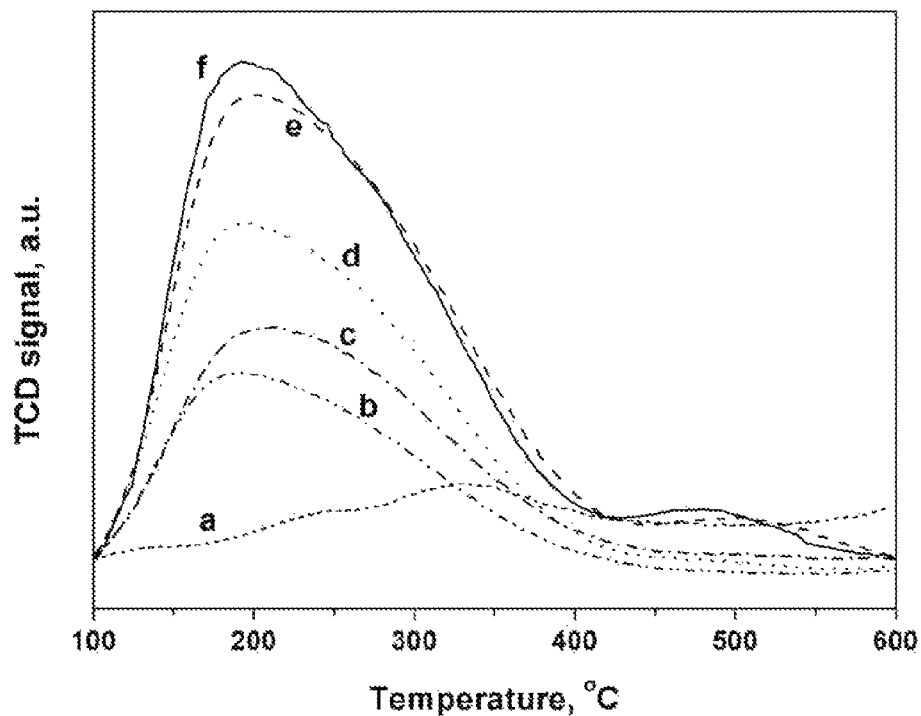
FIG. 11 shows the temperature programmed desorption of ammonia on W-KIT-6 samples with a molar Si/W ratio of (a) infinity, (b) 100, (c) 70, (d) 40, (e) 20, and (f) 10.

Given that tungsten doped mesoporous silicas are known to possess acid sites, we utilized temperature programmed desorption of ammonia ($NH_3$-TPD) to access the acid sites of W-KIT-6 samples (FIG. 11), benchmarking them with siliceous KIT-6. As expected, Si-KIT-6 did not show any appreciable ammonia desorption (0.05 mmol $NH_3$/g). On the other hand, a prominent peak centered around 150-170° C. was observed for W-KIT-6 samples indicating the presence of a large population of weak acid sites. The ammonia desorption peak, and therefore the number of acid sites, increased with higher tungsten loadings (Table 1). Interestingly, a weak desorption peak around 450-500° C., corresponding to strong acid site strength, was noted for the W-KIT-6 (20) and (10) samples.

TABLE 1

Physicochemical properties of calcined W-KIT-6(Si/W) samples.

| Sample[a] | Si/W[b] | $d_{211}$ (nm) | $a_0$[c] (nm) | $S_{BET}$[d] $m^2/g$ | $V_{P, BJH}$[e] cc/g | $d_{P, BJH}$[f] nm | Total Acidity ($NH_3$ mmol/g) |
|---|---|---|---|---|---|---|---|
| W-KIT-6(100) | 104 | 9.75 | 23.9 | 927 | 1.44 | 6.4 | 0.26 |
| W-KIT-6(70) | 78 | 9.78 | 24.0 | 855 | 1.25 | 6.3 | 0.35 |
| W-KIT-6(40) | 45 | 9.71 | 23.8 | 832 | 1.29 | 6.3 | 0.43 |
| W-KIT-6(20) | 22 | 9.95 | 24.4 | 778 | 1.23 | 6.7 | 0.48 |
| W-KIT-6(10) | 12 | 10.14 | 24.8 | 625 | 1.09 | 6.9 | 0.46 |
| Si-KIT-6[g] | ∞ | | | 863 | 1.01 | 6.1 | 0.05 |

[a]numbers in parenthesis represent molar Si/W ratio in synthesis gel
[b]INAA analysis
[c]$a_0 = d_{211}/\sqrt{(h^2 + k^2 + l^2)}$
[d]$S_{BET}$ = Specific Surface Area
[e]$V_{P, BJH}$ = Pore Volume
[f]$d_{P, BJH}$ = Pore Diameter In a separate set of experiments, additional W-KIT-6 catalysts were prepared. The following Table 2 summarizes the physiochemical properties of those samples. Those catalysts were used for the ethylene epoxidation studies of Example 9.

TABLE 2

Physicochemical properties of calcined W-KIT-6(Si/W) samples.

| W-KIT-6 (Si/W) | Si/W | $a_0$ (nm) | $S_{BET}$ $M^2/g$ | $V_{P, BJH}$ cc/g | $d_{P, BJH}$ nm |
|---|---|---|---|---|---|
| W-KIT-6(100) | 114 | 23.9 | 927 | 1.44 | 6.4 |
| W-KIT-6(40) | 57 | 23.8 | 832 | 1.29 | 6.3 |
| W-KIT-6(20) | 24 | 24.4 | 778 | 1.23 | 6.7 |
| W-KIT-6(10) | 17 | 24.8 | 625 | 1.09 | 6.9 |

Example 3

Synthesis of Ce-TUD-1

Figure 12:
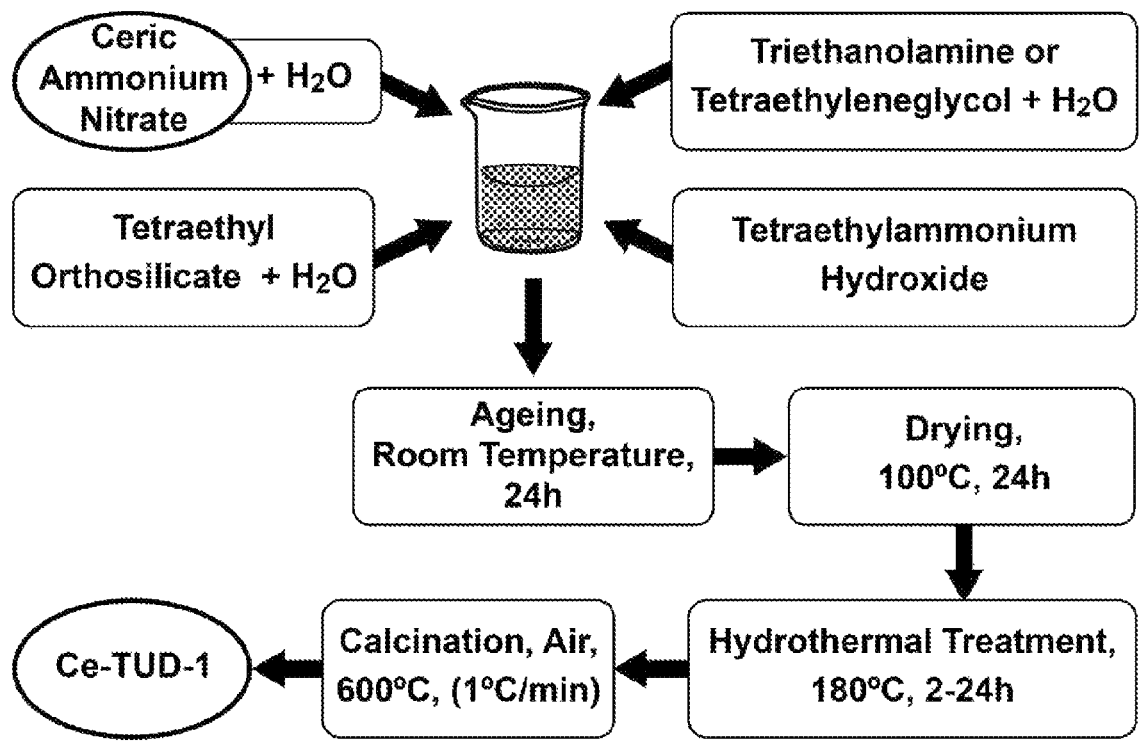
FIG. 12 is a scheme outlining the synthesis of Ce-TUD-1.

An overview of the synthesis of Ce-TUD-1 is illustrated in FIG. 12. The synthesis of Ce-TUD-1 was performed similar to siliceous TUD-1. In a typical synthesis, Ce salt (ceric ammonium nitrate, cerium (III) chloride, or cerium(III) acetate) was dissolved in minimum quantity of deionized water. Then, a mixture of triethanolamine (TEA) and deionized water was added to the ceric ammonium nitrate solution and stirred vigorously for 30 minutes (to avoid vigorous exothermic reaction of ceric ammonium nitrate with TEOS, cerium(III) chloride or cerium(III) acetate may be preferred). To this mixture, required amount of tetraethyl orthosilicate (TEOS, Aldrich) was added and the stirring continued for another 30 minutes. Finally, tetraethyl ammonium hydroxide (TEAOH, 35%, Sigma-Aldrich) was added dropwise to the above mixture and the stirring was continued for another 2 hours. The resulting gel has the following molar composition: 1 $SiO_2$:(0.01-0.1) Ce:(0.35-0.5) TEAOH:1 TEA:11 $H_2O$. This gel was aged at room temperature for 24 hours following by drying at 100° C. for 24 hours. The resulting solid was then transferred into a Teflon lined autoclave for hydrothermal treatment at 160° C. for 16 hours. Finally, the template was removed by calcination in air at 600° C. for 10 hours with a heating rate of 1° C./min.

Example 4

Characterization of Ce-TUD-1

Figure 13:
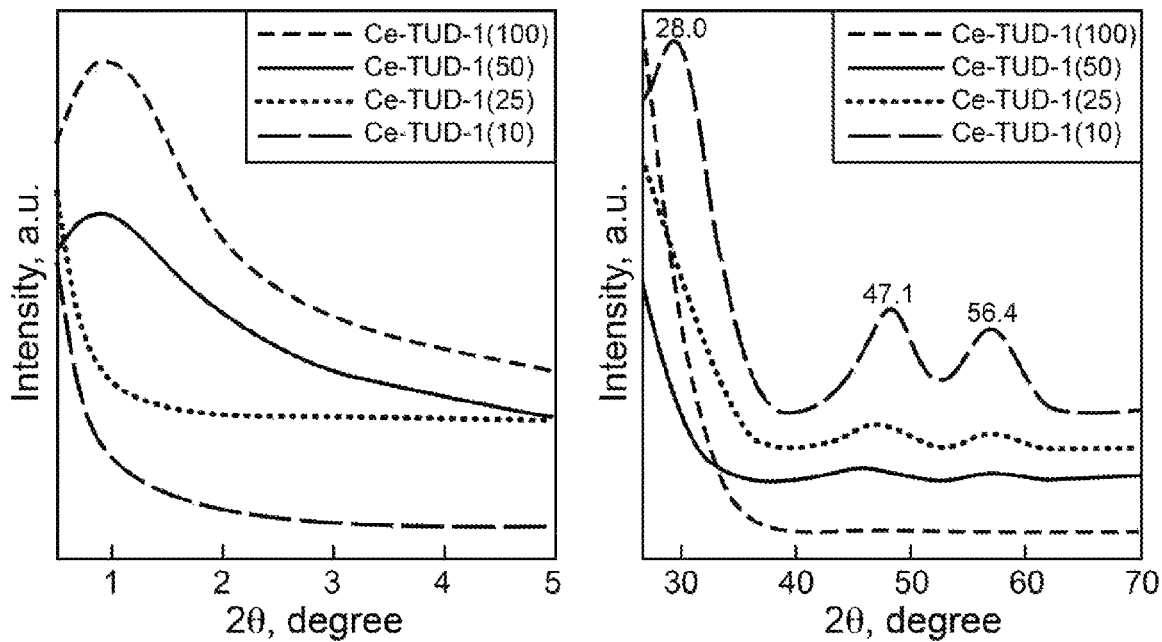
FIG. 13 shows the (left panel) low angle and (right panel) high angle XRD patterns of Ce-TUD-1 samples and (the numbers in parentheses indicate the Si/Ce ratios).

Low angle XRD (0.5-5°) pattern of Ce-TUD-1 (Si/Ce=100 and 50) samples showed a broad intense peak at 2θ value of 0.5-1.0 (FIG. 13, left panel) indicating the mesoporous structure of these materials. No significant peaks were observed for Ce-TUD-1 with Si/Ce ratio of 20 and 10) samples implying that the higher Ce loadings may be affecting the mesostructural nature of this type of materials. Such interference by high transition metal loadings in TUD-1 materials has been previously reported (see Maheswari et al., *Copper containing TUD-1: synthesis, characterization and catalytic behavior in liquid-phase oxidation of ethylbenzene*, J. Porous Mater. 19 103-110 (2012) and Hamdy et al., *Fe, Co and Cu-incorporated TUD-1: Synthesis, characterization and catalytic performance in N2O decomposition and cyclohexane oxidation*, Catal Today 110 264-271 (2005). Also, the peak position and intensity do not follow any trend implying high irregularity in the pore distribution of these materials. The incorporation of cerium cannot be verified by the low angle XRD.

In the high angle XRD (20-80°) spectra (FIG. 13, right panel), a hump observed at 20-22° is attributed to the amorphous nature of Ce-TUD-1. No peaks at higher angle corresponding to $CeO_2$ crystallites were observed in Ce-TUD-1 (100). The reflections observed at 2θ values of 28.0, 47.1, and 56.4° for Ce-TUD-1(10) are attributed to $CeO_2$ (see Li et al., *Direct synthesis of $CeO_2/SiO_2$ mesostructured composite materials via sol-gel process*, Microporous Mesoporous Mat. 120 421-425 (2009)). The peaks at 47.1° and 56.4° were noticed in Ce-TUD-1 with Si/Ce ratio of 50 and 20 and their intensity increases with an increase in Ce content. These results suggest that $CeO_2$ is present at all cerium loadings except Ce-TUD-1 (100) sample.

Figure 14:
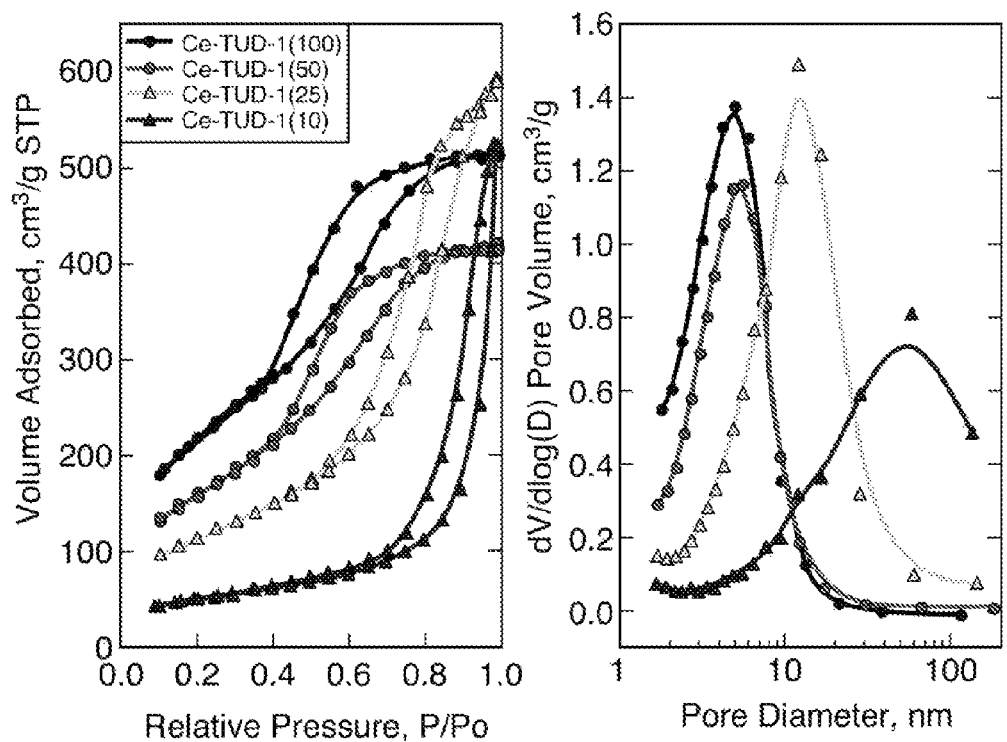
FIG. 14 shows the nitrogen adsorption desorption isotherm (left panel) and pore size distributions (right panel) of Ce-TUD-1 samples.

The mesoporous nature of Ce-TUD-1 samples is confirmed by nitrogen sorption studies (FIG. 14). Ce-TUD-1 showed Type IV adsorption isotherm typical of TUD-1 type mesoporous structures (see Telalovic et al., *TUD-1: synthesis and application of a versatile catalyst, carrier, material etc.*, Mater Chem 20 642-658 (2010)). Ce-TUD-1 (Si/Ce=100, 50 and 20) displayed $H_2$ type hysteresis, signifying the existence of pore distributions without well-defined size and shape. In contrast, Ce-TUD-1 (Si/Ce=10) displayed Type $H_3$ hysteresis loops corresponding to no limiting adsorption at high relative pressure due to slit-shaped pores. The BET surface area of Ce-TUD-1 drastically decreased from 749 $m^2/g$ to 173 $m^2/g$ with an increase in cerium content. Average pore diameter increases from 3.9 to 16.7 nm with an increase in cerium content. The corresponding pore volume of these samples was observed to be between 0.78-0.91 cc/g (see Table 3).

Figure 15:
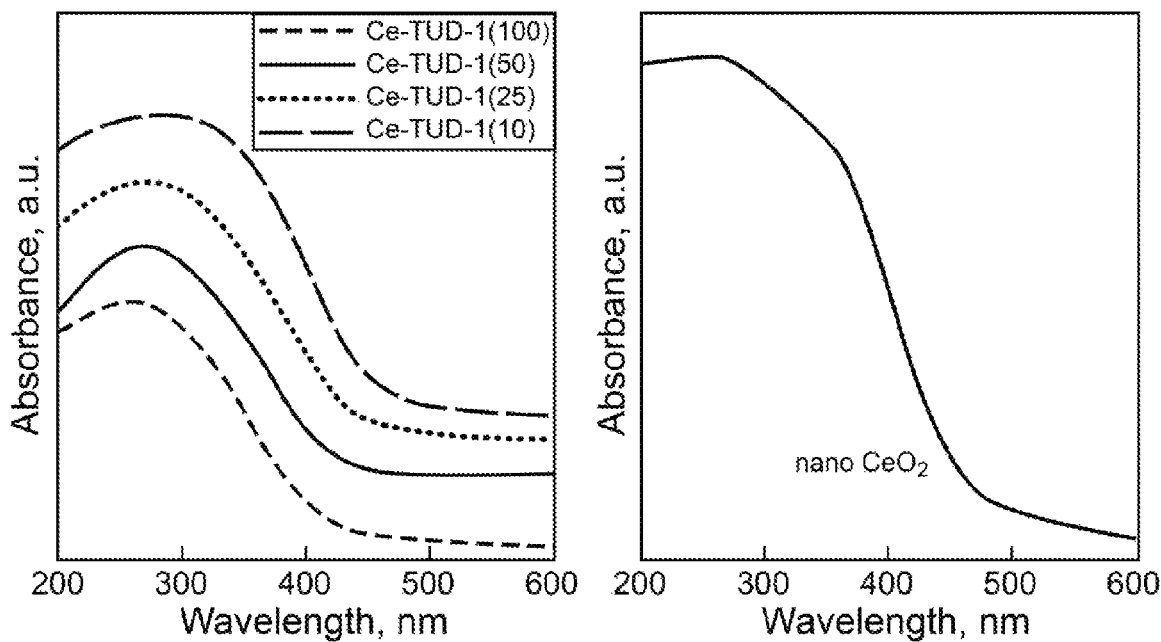
FIG. 15 shows the diffuse reflectance UV-Vis of Ce-TUD-1 samples.

The presence of metal ion in framework or extraframework coordination can be identified by DR-UV-Vis spectroscopy which is known to be a sensitive probe for this type of characterization. FIG. 15 shows diffuse reflectance UV-vis spectra of calcined Ce-TUD-1 samples compared with the spectrum of commercial nano-CeO$_2$. All Ce-TUD-1 samples show a single peak centered around 265 nm. The intensity of this peak increases with cerium amount. Additionally, red shift of this peak center and peak broadening were noticed at higher Ce loadings. The absorption band at 265 nm is attributed to the charge transfer transitions of O$^{2-}$→Ce$^{3+}$ (see Bensalem et al., *From bulk CeO$_2$ to supported cerium-oxygen clusters: a diffuse reflectance approach*, J. Chem. Soc., Faraday Trans. 88 153-154 (1992) and Dai et al., *Direct synthesis of Cerium(III)-incorporated SBA-15 mesoporous molecular sieves by two-step synthesis method*, Microporous Mesoporous Mater. 100 268-275 (2007)). The position of the ligand to metal charge transfer (O$^{2-}$→Ce$^{4+}$) spectra depends on the ligand field symmetry surrounding the Ce center. It has been reported that the charge transfer transitions of O$^{2-}$→Ce$^{4+}$ is observed at 300 nm and hexacoordinated CeO$_2$ is observed at around 400 nm (see Laha et al., *Cerium Containing MCM-41-Type Mesoporous Materials and their Acidic and Redox Catalytic Properties*, J. Catal. 207 213-223 (2002) and Yao et al., *Liquid oxidation of cyclohexane to cyclohexanol over cerium-doped MCM-41*, J. Mol. Catal. A: Chem 246 162-166 (2006)). The DR-UV-Vis spectra of commercial nano-CeO$_2$ shows two peaks at 280 and 353 nm. It has been reported that bulk CeO$_2$ exhibits a strong group of peaks composed of two maxima near 275 nm and 350 nm (see Bensalem et al., *From bulk CeO$_2$ to supported cerium-oxygen clusters: a diffuse reflectance approach*, J. Chem. Soc., Faraday Trans. 88 153-154 (1992)). Hence, we postulate that Ce is incorporated into Ce-TUD-1 as primarily Ce$^{3+}$ with tetra- and hexa-coordinated Ce$^{4+}$ also likely co-existing at higher Ce loadings. It has been reported that both Ce$^{4+}$ and Ce$^{3+}$ coexist, however their relative intensities depend on cerium salt precursor and the treatment atmosphere (see Bensalem et al., *From bulk CeO$_2$ to supported cerium-oxygen clusters: a diffuse reflectance approach*, J Chem Soc, Faraday Trans. 88 153-154 (1992) and Timofeeva et al., *Ce-silica mesoporous SBA15-type materials for oxidative catalysis: Synthesis, characterization, and catalytic application*, Appl Catal A. 317 1-10 (2007)). However, no independent peaks responsible for CeO$_2$ could be resolved in the UV-Vis spectra suggesting that the amount of these species may be very low. The result of DRS-UV-vis spectra is in agreement with high angle XRD analysis.

Figure 16:
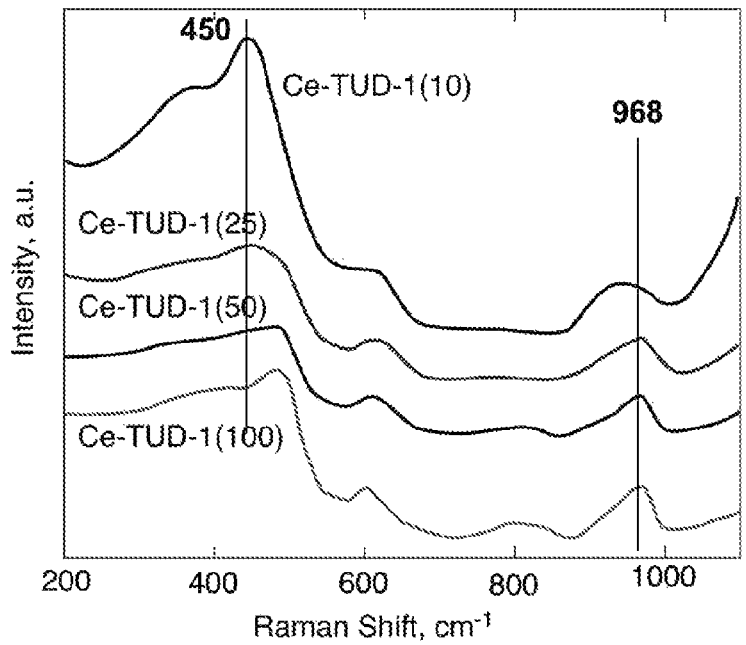
FIG. 16 shows the Raman spectra of Ce-TUD-1 samples.

FIG. 16 shows the results of Raman spectra of Ce-TUD-1 samples with different $n_{Si}/n_{Ce}$ ratios. The Raman bands observed at around 490 cm$^{-1}$, 600 cm$^{-1}$, and 800 cm$^{-1}$ are assigned to silica (see Strunk et al., *Synthesis of Different CeO$_2$ Structures on Mesoporous Silica and Characterization of Their Reduction Properties*, J. Phys. Chem. C 115 4114-4126 (2011)). A prominent peak centered around 450 cm$^{-1}$ was observed for Ce-TUD-1 (10 and 25) samples. In addition, the intensity of this peak increases with cerium loading. CeO$_2$ exhibits a strong and sharp peak centered at 465 cm$^{-1}$ in the Raman spectra and this peak is red shifted with a decrease in CeO$_2$ particle size (see Yang et al., *Size-Dependent Raman Red Shifts of Semiconductor Nanocrystals*, J. Phys. Chem. B 112 14193-14197 (2008) and Scholes et al., *Influence of Hydrogen Peroxide in the Preparation of Nanocrystalline Ceria*, Chem. Mater. 19 2321-2328 (2007)). The band at 968 cm$^{-1}$ observed in all Ce-TUD-1 samples may be attributed to Si—O—Ce (see Laha et al., *Cerium Containing MCM-41-Type Mesoporous Materials and their Acidic and Redox Catalytic Properties*, J. Catal. 207 213-223 (2002)).

TABLE 3

Characteristics of Ce-TUD-1 (Si/Ce ratio)

| Sample[a] | Si/Ce | Ce (wt %) | $S_{BET}$ m$^2$/g | $V_{P, BJH}$ cc/g | $d_{P, BJH}$ nm |
|---|---|---|---|---|---|
| Ce-TUD-1 (100) | 113 | 2 | 749 | 0.78 | 3.9 |
| Ce-TUD-1 (50) | 45 | 5 | 587 | 0.65 | 4.3 |
| Ce-TUD-1 (25) | 21 | 10 | 406 | 0.91 | 9.4 |
| Ce-TUD-1 (10) | 7 | 25 | 173 | 0.79 | 16.7 |

$S_{BET}$ = Specific Surface Area,
$V_{P,BJH}$ = Pore Volume,
$d_{P,BJH}$ = Average Pore Diameter Example 5

Synthesis of Nb-KIT-6

Figure 17:
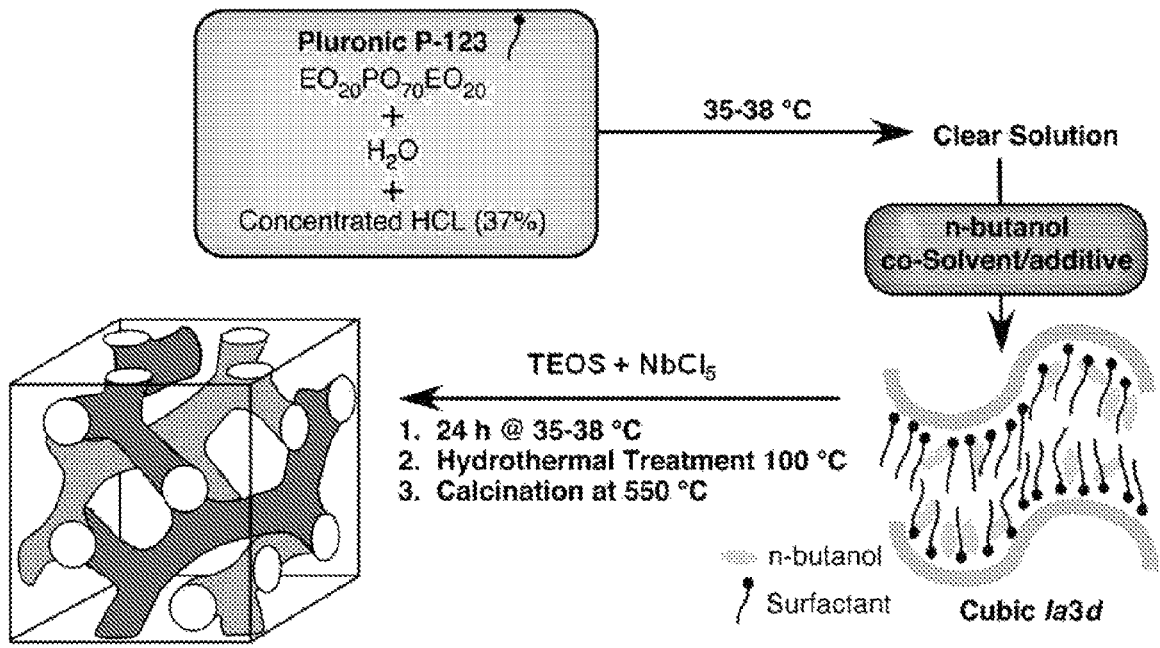
FIG. 17 is a scheme outlining the synthesis of Nb-KIT-6.

Nb-KIT-6 materials with different Si/Nb atomic ratios were synthesized using Pluronic P123 tri-block co-polymer as a structure-directing agent and n-butanol as additive for cubic Ia3d mesophase formation. In a typical synthesis, 5.0 g of P123 was dissolved in 190 g 0.5 M hydrochloric acid solution at 35° C. After complete dissolution, 5.0 g of n-butanol was added and the resulting mixture was stirred for another 1 hour at 35° C. Finally, to this mixture, 10.6 g of TEOS and the required amounts of niobium (V) chloride were added and the stirring was continued for another 24 hours. Subsequently, the reaction mixture was transferred to a 300 ml Teflon lined SS autoclave and heated for 24 hours at 100° C. under static condition for hydrothermal treatment. The solid product was filtered off without washing and then dried at 100° C. overnight. The structure-directing agent was removed by calcination in a flow of dry air at 550° C. for 5 hours. An overview of the synthesis scheme is illustrated in FIG. 17.

Example 6

Characterization of Nb-KIT-6

2-D SAXS (Small Angle X-ray Scattering) patterns of Nb-KIT-6 samples were collected on a Rigaku system with a S-MAX 3000 instrument using a Bede Scientific microfocus tube source operating at 45 kV and 0.66 mA. Patterns were rotationally averaged and presented as intensity vs. scattering angle. A 10 cm×10 cm wire detector was placed approximately 150 cm from the sample position and silver behenate was used to determine the exact pixel to scattering angle conversion. X-ray powder diffraction (XRD) patterns in the high angle (2θ=10-80°) were collected on a Bruker Proteum Diffraction System equipped with Helios multilayer optics, an APEX II CCD detector and a Bruker MicroStar microfocus rotating anode x-ray source operating at 45 kV and 60 mA.

Nitrogen adsorption-desorption isotherms were measured at −196° C. on a Quantachrome NOVA 2000e sorption analyzer. Prior to the physisorption experiment, the samples were heated in vacuum at 300° C. for 1 hour. Elemental analysis was carried out by digesting the samples in HF and H$_2$SO$_4$ mixture and analyzed on a Horiba Jobin Yvon JY 2000 (ICP-OES) instrument. Raman spectra of Nb-KIT-6 powder samples were acquired on a SENTERRA (Bruker) dispersive Raman microscope equipped with a thermoelectrically cooled CCD detector and an Argon laser.

Diffuse reflectance UV-Vis spectra were collected in the 200-800 nm range at room temperature, using Spectralon as the reference, with a PerkinElmer (Lambda 850) spectrophotometer equipped with a diffuse reflectance integrating sphere."

Solid state NMR spectra were acquired on a Bruker Avance III 400 spectrometer (Bruker Biospin, Billerica, Mass.) operating at 400.1 MHz for $^1$H and 79.49 MHz for Si. A 7 mm spin module in a 4-module multiple sample solids (MSS) probe (Revolution NMR, Ft. Collins, Colo.) was used. Spectrometer setup used sodium 3-(trimethylsilyl)-propionate (TSP) as a secondary external chemical shift reference at 1.44 ppm relative to TMS. Each sample was packed into a 7.0 mm zirconia rotor (Revolution NMR, Ft. Collins, Colo.). The rotors were closed with Kel-F end caps. Magic angle spinning used at sample spinning rate of 4 kHz. Cross polarization (CP) was used for all measurements using a contact time of 4.0 ms. A pulse delay of 1.0 s was used. The spectral width was 30 kHz and the acquisition time was 15 ms. Proton decoupling was performed with SPINAL-64 and a proton decoupling field of 64 kHz. Each data set is the sum of 3600 transients.

Temperature programmed Reduction (H$_2$-TPR) and Temperature programmed desorption of ammonia (NH$_3$-TPD) was carried out with a Micromeritics Autochem 2910 instrument equipped with a Thermal Conductivity Detector (TCD). For H$_2$-TPR, about 50-100 mg of Nb-KIT-6 sample is loaded in the sample tube and heated to 550° C. in a flow of Argon and subsequently cooled to ambient temperature. Then H$_2$/Ar mixture is flown through the tube and the temperature was raised to 1050° C. at a ramp of 10° C./min and the consumption of hydrogen was monitored using TCD detector. For NH$_3$-TPD, about 50-100 mg of Nb-KIT-6 samples were heated from room temperature to 550° C. to remove adsorbed water and were cooled down immediately to 100° C. in a flow of helium (30 sccm). Ammonia was adsorbed at this temperature for 30 minutes from a He stream containing 9.98 vol % NH$_3$ flowing at 30 sccm. Then the gas flow was switched to helium (30 sccm) and continued for another 30 minutes in order to remove any physisorbed ammonia. Following this step, the temperature was raised from 100° C. to 550° C. at a ramp of 10° C./min and the desorbed ammonia was recorded.

Figure 18:
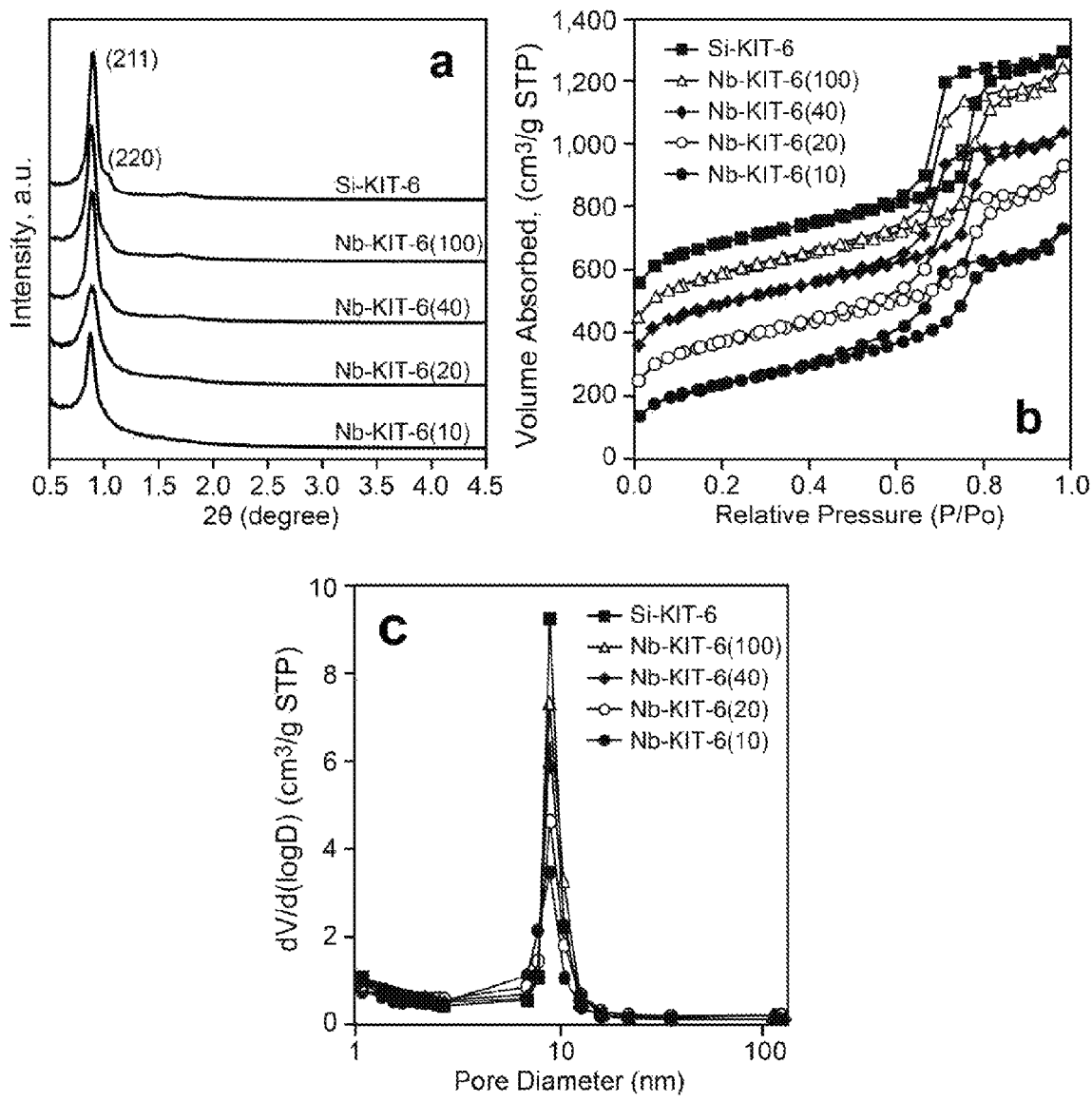
FIG. 18 shows the small angle X-ray scattering patterns of (a) nitrogen sorption isotherms (b) and pore size distributions (c) of calcined Nb-KIT-6 (Si/Nb=10, 20, 40, and 100) samples.

Nb-KIT-6 samples exhibit the typical XRD patterns which are indexed to the (211) and (220) reflections of a cubic three-dimensional mesostructure with Ia3d symmetry (FIG. 18a). A significant decrease in structural ordering was observed by incorporation of higher amounts of niobium into the KIT-6 framework. Compared to pristine KIT-6, a marginal shift of the (211) reflection peaks to lower 2θ values with increasing Si/Nb atomic ratio was observed. This is attributed to an increase in the unit cell parameter ($a_0$) caused by the incorporation of the Nb ions in the framework of KIT-6.

The nitrogen adsorption-desorption isotherms of the Nb-KIT-6 samples (FIG. 18b) exhibit a Type IV isotherm with a well-defined sharp inflexion at a relatively high partial pressure of 0.7-0.8. This is due to capillary condensation of nitrogen. The H1-type hysteresis loop observed for all Nb-KIT-6 samples indicates uniformity of pores which is further confirmed by the pore size distribution curves (FIG. 18c). The BET specific surface area and total pore volume decreased from 997 to 804 m$^2$/g and 1.46 to 1.12 cm$^3$/g with an increase in niobium content from Si/Nb=100 to Si/Nb=10, respectively. The pore sizes of Nb-KIT-6 samples estimated by BJH model is around 9.3 nm and the wall thickness (estimated using the equation W=$a_0$/2–D$_{P,DFT}$) was found to be around 3.8-3.9 nm (Table 4).

TABLE 4

Physical and Textural Properties of Nb-KIT-6 Samples..

| Sample$^a$ | Si/Nb$^b$ (Nb wt %) | $a_0^c$ nm | $S_{BET}^d$ m$^2$/g | $V_{P,BJH}^e$ cm$^3$/g | $d_{P,BJH}^f$ nm | $D_{P,DFT}$ nm | W$^g$ nm | Total acidity NH$_3$ mmol/g |
|---|---|---|---|---|---|---|---|---|
| Si-KIT-6 | ∞ | 24.1 | 1013 | 1.38 | 9.3 | 8.5 | 3.6 | 0.04 |
| Nb-KIT-6(100) | 98 (1.5) | 24.4 | 997 | 1.46 | 9.3 | 8.5 | 3.8 | 0.27 |
| Nb-KIT-6(40) | 41 (3.4) | 24.4 | 991 | 1.29 | 9.3 | 8.5 | 3.8 | 0.36 |
| Nb-KIT-6(20) | 21 (6.1) | 24.4 | 926 | 1.28 | 9.3 | 8.5 | 3.8 | 0.51 |
| Nb-KIT-6(10) | 9.8 (10.9) | 24.7 | 804 | 1.12 | 9.3 | 8.5 | 3.9 | 0.75 |

Figure 19:
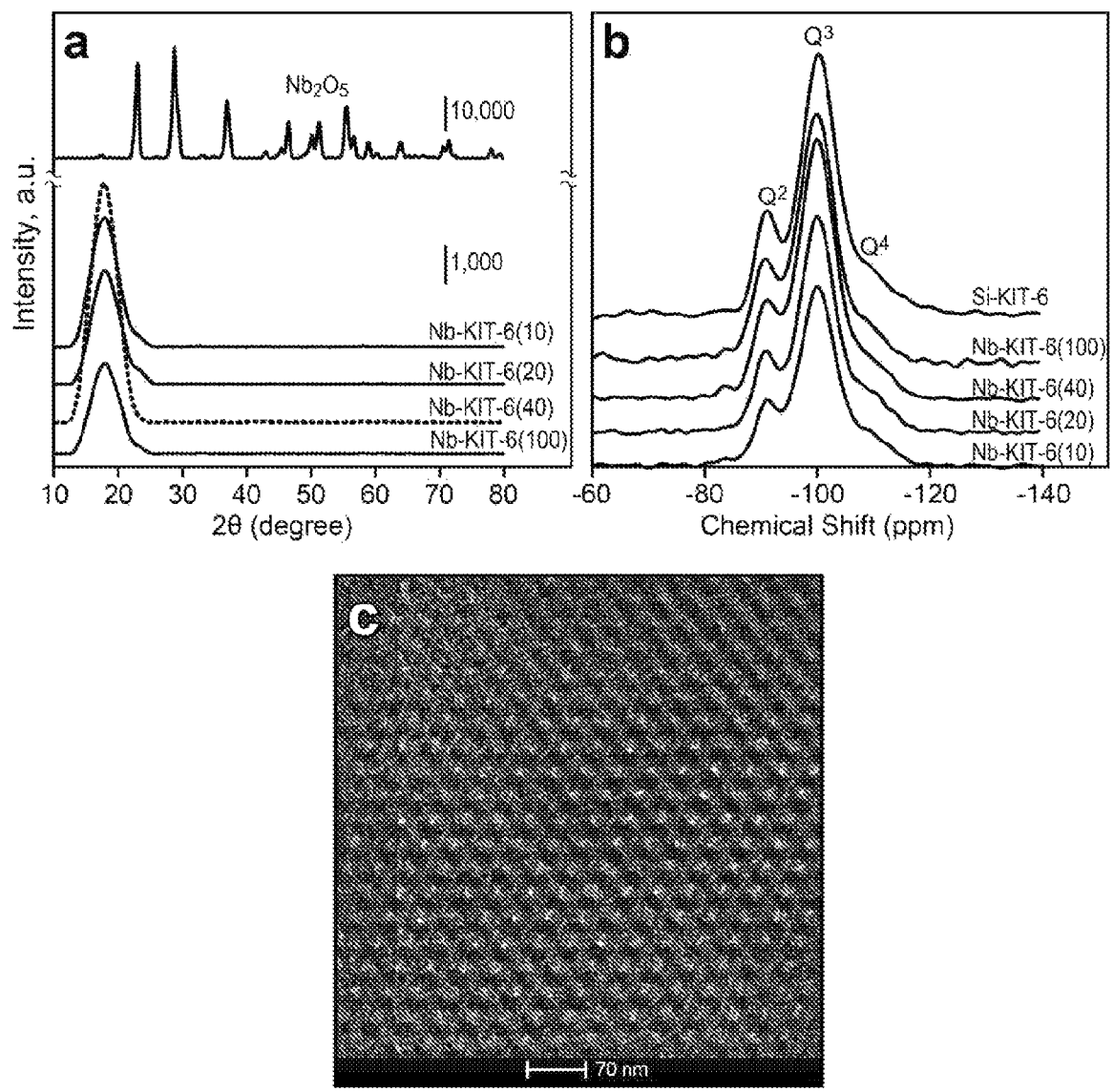
FIG. 19 shows the high angle powder XRD patterns (a) Si MAS-NMR spectra, (b) and representative TEM image, (c) of calcined Nb-KIT-6 (Si/Nb) samples.

$^a$Numbers in parenthesis represent Si/Nb ratio in synthesis gel.
$^b$ICP-OES analysis.
$^c a_0 = d_{211}/\sqrt{(h^2 + k^2 + l^2)}$
$^d S_{BET}$ = Specific Surface Area calculated from the adsorption branch of the isotherm in the relative pressure range of 0.05-0.25 using BET model
$^e V_{P,BJH}$ = Total Pore Volume measured at P/P$_o$ = 0.98.
$^f d_{P,BJH}$ = BJH adsorption Pore Diameter.
$^g$W = wall thickness evaluated by $a_0$/2 – D$_{P,DFT}$.
D$_{P,DFT}$ is the mesopore diameter calculated using NLDFT kernel developed for equilibrium capillary condensation isotherms of N$_2$ at 77 K on silica Interestingly, for all Nb-KIT-6 samples, a broad peak around 15-25° 2θ was observed due to amorphous silica and no reflections corresponding to Nb$_2$O$_5$ were observed even for the highest Nb content sample, Nb-KIT-6(10) (FIG. 19a). It is plausible that the niobium oxide species in these materials are either uniformly well dispersed on the mesopore walls or the Nb$_2$O$_5$ phase did not arrange in a well-ordered manner. We also carried out H$_2$-TPR and no reduction peaks were observed in the temperature range studied (50 to 1050° C.), again indicating a high dispersion and strong interaction of niobium species with KIT-6 silica matrix. Si MAS-NMR spectra of the Nb-KIT-6 samples compared with pristine KIT-6 sample (FIG. 19b) show three signals with chemical shifts near −90°, −100°, and −110 ppm. These signals are assigned to disilanol [Q$^2$, Si(OR)$_2$(OSi)$_2$], silanol [Q$^3$, Si(OR)(OSi)$_3$] and fully interconnected silicate groups [Q$^4$, Si(OSi)$_4$] respectively (where R═H and/or Nb). The relative fractions of Q$^2$, Q$^3$, and Q$^4$ silicon species present in Nb-KIT-6 and siliceous KIT-6 samples are given in Table 4A. As compared to Si-KIT-6, all Nb-KIT-6 samples [except Nb-KIT-6(10)] showed an increase in Q$^3$/Q$^4$ or (Q$^2$+Q$^3$)/Q$^4$ silicon fraction values suggesting that Si ions are replaced by Nb ions in the framework positions. On the other hand, these values are significantly reduced for Nb-KIT-6(10) sample. This could be due to segregation of Nb species instead of framework incorporation. High resolution TEM representative image of Nb-KIT-6 (FIG. 19c) also confirms the highly structural ordering in these samples.

TABLE 4A $^{29}$Si MAS NMR analysis of Nb-KIT-6 samples compared with Si-KIT-6

| Sample | Q² | Q³ | Q⁴ | (Q² + Q³)/Q⁴ | Q³/Q⁴ |
|---|---|---|---|---|---|
| Nb-KIT-6(10) | 17.04 | 59.53 | 23.44 | 3.27 | 2.54 |
| Nb-KIT-6(20) | 19.02 | 63.54 | 17.44 | 4.73 | 3.64 |
| Nb-KIT-6(40) | 19.06 | 66.96 | 12.83 | 6.70 | 5.22 |
| Nb-KIT-6(100) | 20.72 | 67.83 | 11.46 | 7.73 | 5.92 |
| Si-KIT-6 | 17.83 | 64.23 | 17.94 | 4.57 | 3.58 |

Figure 20:
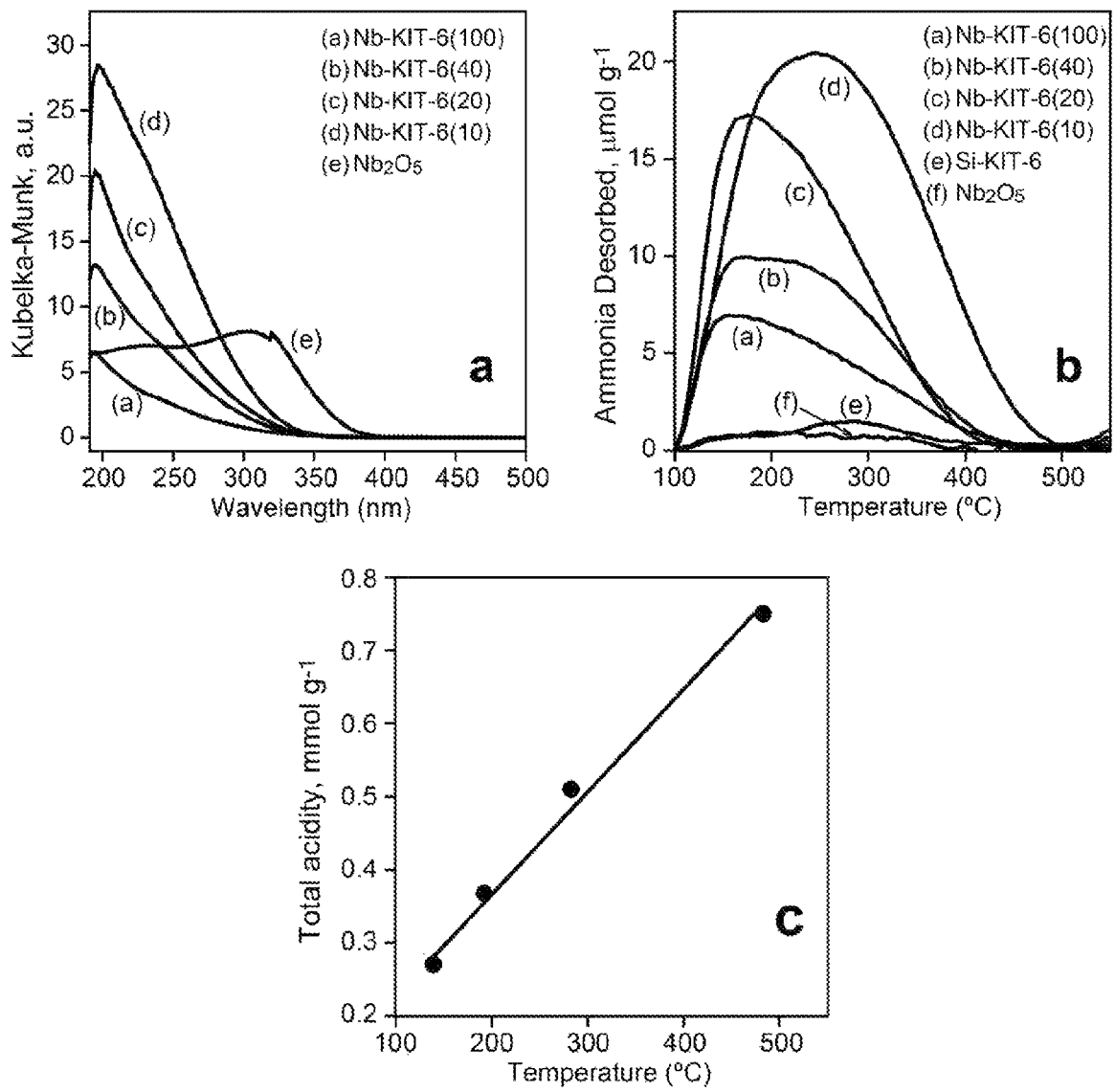
FIG. 20 shows (a) diffuse reflectance UV-Vis spectra, (b) temperature programmed desorption of ammonia, and (c) almost linear dependency of total acidity of Nb-KIT-6 materials with Nb content.
Figure 21:
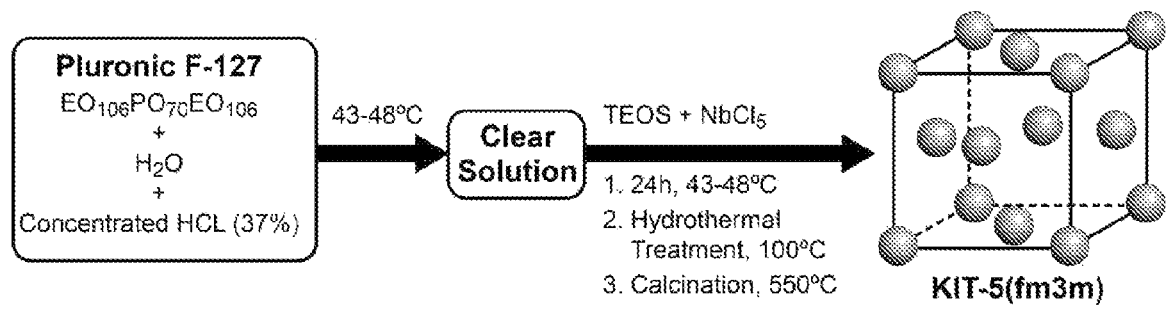
FIG. 21 is a scheme outlining the synthesis of Nb-KIT-5.

Diffuse reflectance UV-Vis spectra of Nb-KIT-6 samples showed a well-defined absorption peak near 195 nm and a shoulder around 235-240 nm (FIG. 20a). The peak around 195 nm is slightly red-shifted with an increase in the Nb content. Moreover, the intensities of both these absorption bands increased monotonically with an increase in the Nb content. Absorption maxima near 200 nm and 240 nm were reported for niobium containing materials such as NbS-1, NbAPO-5, and Nb-SBA-15. The absorption maximum observed near 195 nm can be assigned to ligand to metal charge transfer arising from excitation of an oxygen 2p electron in the valance band to the empty orbital of the Nb ions surrounded by the oxygen ($NbO_4$ tetrahedra units). It has also been reported that a transition with two maxima near 220 nm and 270 nm was observed for highly dispersed niobium oxide on silica, which are assigned to monomeric and oligomeric $NbO_4$ tetrahedra. It is generally accepted that a blue shift of absorption bands is observed with a decrease in the particle size of oxide particles. Hence, the peak around 240 nm may be assigned to charge transfer transition between the tetrahedral oxygen ligands and the central Nb ions in the mononuclear tetrahedral $NbO_4$ with a higher coordination number. For commercial $Nb_2O_5$ powder, the main absorption band was observed around 310 nm. The lack of this band in Nb-KIT-6 samples suggests that most of the Nb ions are framework-incorporated in the KIT-6 silica matrix at lower Nb content with an increase in oligomeric $NbO_4$ tetrahedra at higher Nb content without any formation of crystalline $Nb_2O_5$. These conclusions are in agreement with the XRD analysis.

The incorporation of niobium into mesoporous silicates might impart acidity to the framework and both types of acid sites (Brønsted and Lewis) have been reported for Nb-SBA-15 materials with Lewis acid sites being the majority. We have evaluated the total amounts of acid sites present in Nb-KIT-6 by $NH_3$-TPD. For comparison, pristine KIT-6 and bulk $Nb_2O_5$ were considered and the results are shown in FIG. 20b. Negligible acidity was observed in the case of bulk $Nb_2O_5$ and Si-KIT-6. However, with the introduction of niobium ions in KIT-6 framework, acidity was observed which increased with niobium content. The linearity in total number of acid sites and the amount of niobium species (Nb/Si ratio) in the sample also suggests that niobium is mostly framework incorporated at all loadings studied (FIG. 20c). These results are complementary to high angle XRD and diffuse reflectance UV-Vis.

Example 7

Synthesis of Nb-KIT-5

The synthesis of Nb-KIT-5 materials was carried out following the procedure reported for synthesizing high quality siliceous KIT-5 material (see Kleitz et al., *Large Cage Face-Centered-Cubic Fm3m Mesoporous Silica: Synthesis and Structure*, J. Phys. Chem. B 107 14296-14300 (2003)). In a typical synthesis, 3.6 g of triblock copolymer Pluronic F127 (Sigma) were dissolved in 180 ml of 0.4 M HCl solution at 45° C. Then 16.9 g of tetraethyl orthosilicate (TEOS 98%, Aldrich) and required amounts of niobium chloride (Aldrich) were added. The resulting reaction mixture was stirred at 45° C. for 18 h and then hydrothermally treated at 98° C. for 24 h under static conditions in a Teflon-lined stainless steel autoclave. The solid product was filtered without washing, dried at 100° C. overnight and calcined in a flow of air at 550° C. for 5 hours. The resulting solids are denoted as Nb-KIT-5 (molar Si/Nb ratio).

Example 8

Characterization of Nb-KIT-5

Figure 22:
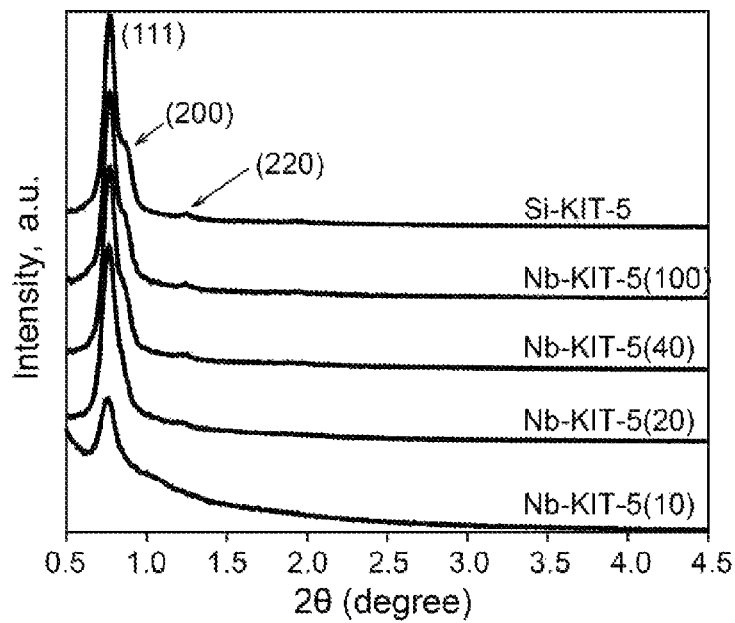
FIG. 22 shows the small angle X-ray scattering patterns of calcined Nb-KIT-5 (Si/Nb=10, 20, 40, and 100) samples compared with Si-KIT-5.

Small-angle X-ray scattering (SAXS) patterns of Si-KIT-5 and Nb-KIT-5 samples exhibited three well-resolved peaks at 2θ values of 0.77, 0.85 and 1.20 degrees as shown in FIG. 22. These reflections are indexed to (111), (200) and (220) planes of cubic Fm3m structure [1-4]. The observed d spacings and the calculated unit cell parameter ($a_0$) are similar to those that of KIT-5 materials. See Anand et al., *Preparation of mesoporous titanosilicate molecular sieves with a cage type 3D porous structure for cyclohexene epoxidation*, Microporous Mesoporous Mater 160 159-166 (2012); Balasubramanian et al., *Highly active three-dimensional cage type mesoporous aluminosilicates and their catalytic performances in the acetylation of aromatics*, Microporous Mesoporous Mater 114 303-211 (2008). This implies that the Nb species are effectively incorporated in the KIT-5 silica matrix, especially at lower Nb contents (i.e., from Si/Nb=100 to 25) which is further confirmed by an increase in unit cell parameter for this sample (see Table 5). In case of samples with higher Nb content, Nb-KIT-5(10) for example, the higher order peaks were not resolved. In addition, a drastic decrease in intensity of the (111) peak was noted. This clarifies the limit of effective Nb incorporation into the KIT-5 matrix.

Figure 23:
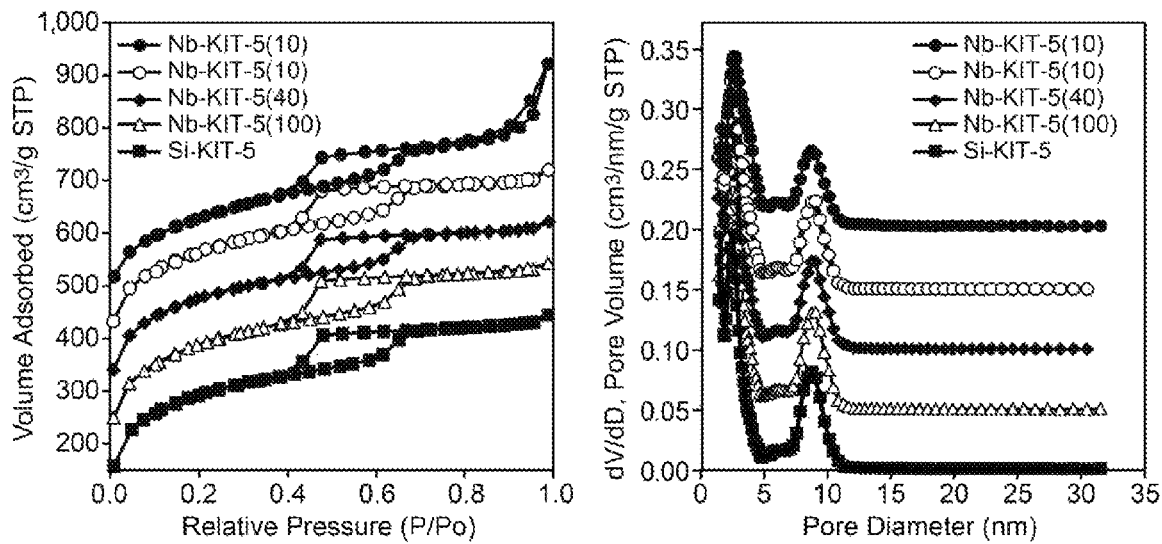
FIG. 23 shows the $N_2$ sorption isotherms of Nb-KIT-5 samples (left panel) and their pore size distribution (right right) determined using NLDFT adsorption branch kernel developed for silica exhibiting cylindrical/spherical pore geometry. The data is shown for Nb-KIT-5 (SiNb=10, 20, 40, and 100) samples.

Nitrogen sorption isotherms of Nb-KIT-5 samples compared with Si-KIT-5 sample are shown in FIG. 23 and the textural parameters of these samples are given in Table 5. All KIT-5 samples showed type IV adsorption isotherm with sharp capillary condensation step between 0.58-0.71 $P/P_0$ and a broad H2-type hysteresis loop with a desorption occurring at about 0.47 $P/P_0$. This indicates that these mesoporous materials possessed ordered pores with large uniform cage-like pores (see Kleitz et al., *Large Cage Face-Centered-Cubic Fm3m Mesoporous Silica: Synthesis and Structure*, J. Phys. Chem. B 107 14296-14300 (2003); Wu et al., *Structural modulation of cage-like mesoporous KIT-5 silica by post-synthesis treatments with ammonia and/or sulfuric acid*, Microporous Mesoporous Mater 117 249-256 (2009); Anand et al., *Preparation of mesoporous titanosilicate molecular sieves with a cage type 3D porous structure for cyclohexene epoxidation*, Microporous Mesoporous Mater 160 159-166 (2012); and Balasubramanian et al., *Highly active three-dimensional cage type mesoporous aluminosilicates and their catalytic performances in the acetylation of aromatics*, Microporous Mesoporous Mater 114 303-211 (2008)). As inferred from Table 5, the specific surface area of Nb-KIT-5 samples decreased from 1022 m²/g to 810 m²/g with an increase in Nb content, whereas, the pore volume was observed to be nearly the same around 0.65-0.69 cm³/g as shown in FIG. 23. The pore size distribution, determined using NLDFT adsorption branch kernel (Autosorb software) developed for silicas that exhibit cylindrical/spherical pore geometry, revealed a bimodal pore size distribution typical of cage-type materials. The entrance diameter of the mesoporous cage is estimated to be 2.5-2.6 nm while the pore diameter of the mesopore cages is estimated to be 8.8 nm which did not vary much with Nb content.

Figure 24:
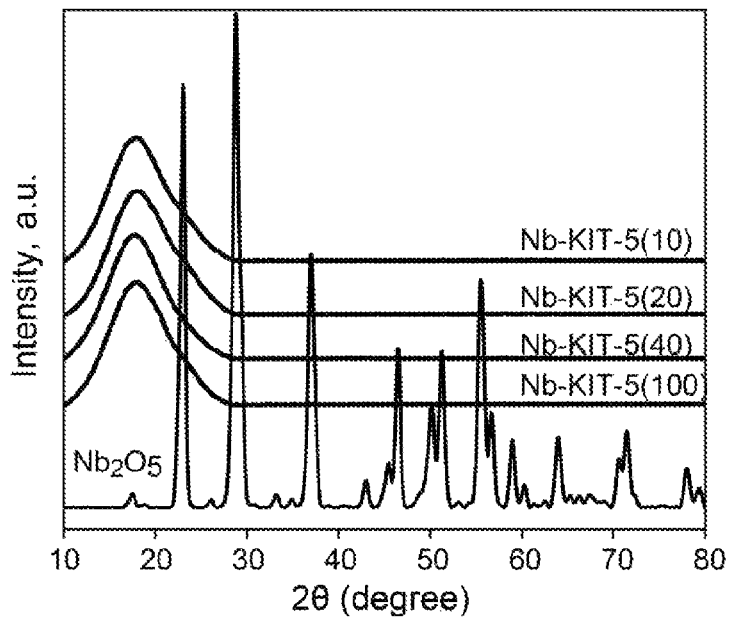
FIG. 24 shows the wide angle XRD powder patterns of Nb-KIT-5 (molar Si/Nb ratio) samples compared with crystalline $Nb_2O_5$.

High-angle XRD of Nb-KIT-5 samples (FIG. 24) showed only a broad peak around 15-25° 2θ, characteristic of amorphous silica. No characteristic reflections of crystalline $Nb_2O_5$ was observed even for the high Nb content sample, Nb-KIT-5(10). Similar observations were also made for niobium doped silica (see Carniti et al., *Dispersed NbOx Catalytic Phases in Silica Matrixes: Influence of Niobium Concentration and Preparative Route*, J. Phys. Chem. C 112 14064-14074 (2008)) and niobium rich SBA-15 type materials (see Trejda et al., *Niobium rich SBA-15 materials—preparation, characterisation and catalytic activity*, Microporous Mesoporous Mater 110 271-278 (2008)). It is suggested that niobium oxide species in these materials are either well dispersed on the mesopore walls or $Nb_2O_5$ phase did not arrange in a well-ordered manner. We also carried out $H_2$-TPR (temperature programmed reduction) for Nb-KIT-5 samples by ramping the sample temperature up to 1050° C. in a flow of 10% $H_2$ in Ar (30 standard cm$^3$/min). No significant hydrogen uptake was measured during this study (not shown). This observation also indicates the absence of niobium in extra framework positions and that the interaction of niobium species with the walls is very strong to observe any $H_2$ consumption during our study.

Figure 25:
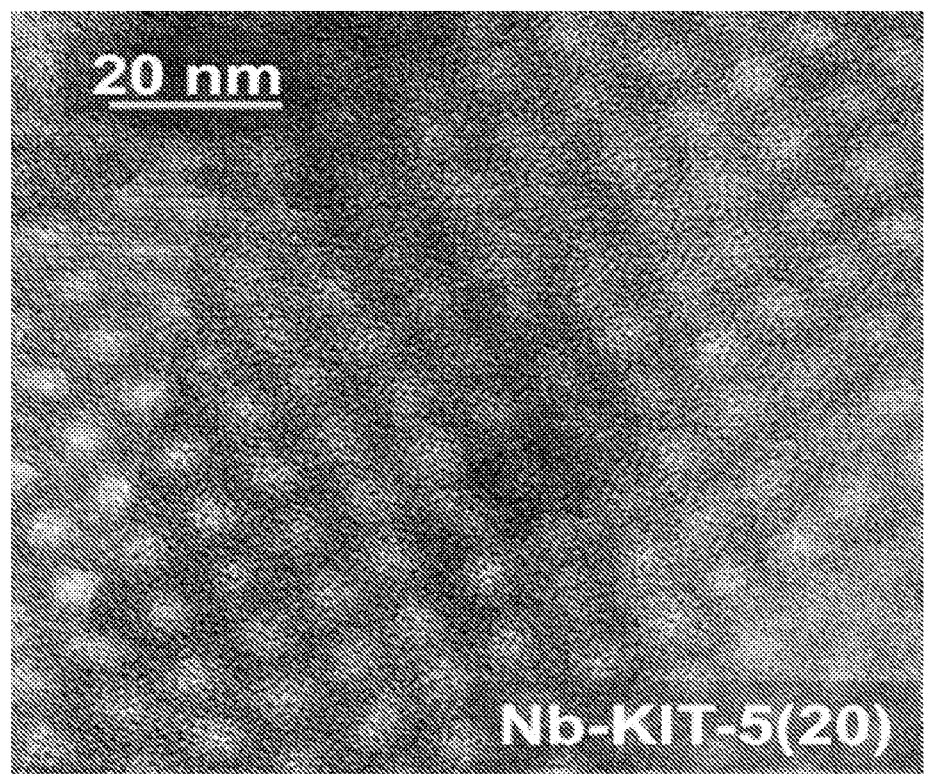
FIG. 25 shows a representative TEM image of calcined Nb-KIT-5 (SiNb=20) samples.

Representative transmission electron microscopy images for Nb-KIT-5 sample is shown in FIG. 25. Cubic three-dimensional mesoporous structure with a high degree of long-range ordering was evident from these images. The size of mesopore cages estimated from line profile in TEM image is in line with $N_2$ sorption studies.

Figure 26:
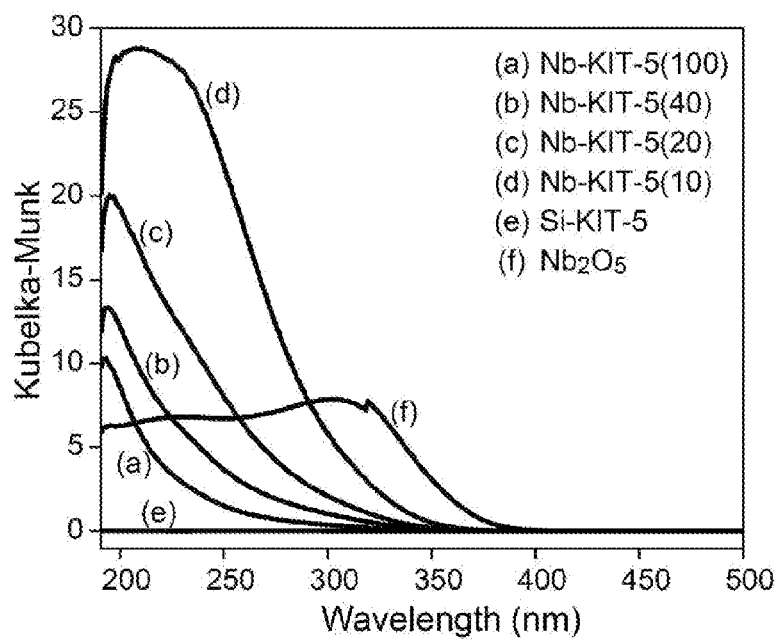
FIG. 26 shows the diffuse reflectance UV-Vis spectra Nb-KIT-5 materials with Nb content.

Diffuse reflectance UV-Vis spectra of Nb-KIT-5 samples showed a well-defined absorption peak near 195 nm and a shoulder around 235-240 nm (FIG. 26). The peak around 195 nm was gradually red-shifted with an increase in the Nb content with monotonic increases in the intensities of both the absorption bands. Absorption maxima near 200 nm and 240 nm were reported for niobium containing materials such as NbS-1 (see Y. S. Ko, H. T. Jang and W. S. Ahn, J Ind Eng Chem, 13 pg. 764 (2007) and Hartmann, *Synthesis of Niobium-and Tantalum-Containing Silicalite-1*, Chem. Lett. 407-408 (1999)), NbAPO-5 (see Hartmann et al., *Characterization and Catalytic Evaluation of Mesoporous and Microporous Molecular Sieves Containing Niobium*, Catal. Today 78 467-475 (2003)) and Nb-SBA-15 (see Srinivasu et al., *Highly ordered two dimensional p6mm mesoporous niobium silicates with high niobium content: "winding road" of regularly aligned nano-channels*, J. Phys. Chem. C 112 10130-10140 (2008)). The absorption maximum observed near 195 nm can be attributed to ligand to metal charge transfer arising from excitation of an oxygen 2p electron in the valence band to the empty orbital of the Nb ions surrounded by the oxygen ($NbO_4$ tetrahedra units). Absorption bands with two maxima around 220 nm and 270 nm have also been reported for highly dispersed niobium oxide on silica, and have been assigned to monomeric and oligomeric $NbO_4$ tetrahedra (see Tanaka et al., *Preparation of highly dispersed niobium oxide on silica by equilibrium adsorption method*, Catal. Today 16 297-307 (1993)). It is generally believed that a blue shift of absorption bands occurs with a decrease in the particle size of oxide particles. Hence, the peak around 240 nm may be assigned to charge transfer transition between the tetrahedral oxygen ligands and the central Nb ions in the mononuclear tetrahedral $NbO_4$ with a higher coordination number. For commercial $Nb_2O_5$ powder the main absorption band was observed around 310 nm and the lack of this band in Nb-KIT-5 samples suggest that most of the Nb ions are framework incorporated in the KIT-5 silica matrix at lower Nb content with an increase in oligomeric $NbO_4$ tetrahedra at higher Nb content without any detectable formation of crystalline $Nb_2O_5$. Thus, it can be summarized that Nb ions are framework incorporated in the KIT-5 silica matrix.

TABLE 5

Physical and Textural Properties of Nb-KIT-5 Samples

| KIT-5 (Si/Nb) | Si/Nb (Nb wt %) | $a_0$ nm | $S_{BET}$ m$^2$/g | $V_{tp}$ cc/g | $V_{mp}$ cc/g | $d_{P, NLDFT}$ nm |
|---|---|---|---|---|---|---|
| Si-KIT-5 | n/a | 19.8 | 1036 | 0.69 | 0.30 | 8.5 |
| Nb-KIT-5(100) | 106 (1.4) | 19.8 | 1022 | 0.69 | 0.30 | 8.8 |
| Nb-KIT-5(40) | 42 (3.3) | 19.8 | 978 | 0.65 | 0.21 | 8.8 |
| Nb-KIT-5(20) | 23 (5.6) | 19.8 | 936 | 0.64 | 0.15 | 8.8 |
| Nb-KIT-5(10) | 11 (10) | 20.2 | 810 | 0.81 | 0.06 | 8.8 |

Example 9

Ethylene Epoxidation Using Catalysts

In this example, epoxidation of ethylene as an exemplary olefin was evaluated using the exemplary catalysts described herein. More specifically, the W-KIT-6, W-KT-5, Nb-KIT-6, Nb-KIT-S, and Ce-TUD-1 catalysts (tungsten, niobium and cerium metal incorporated into the framework of ordered and amorphous silicate supports) were tested for ethylene epoxidation. The experimental conditions were as follows: methanol (solvent) 20 g; 50 wt % $H_2O_2/H_2O$(Oxidant)=8 g; acetonitrile (Internal Standard)=0.9 g; reactor pressure=50 bar; agitation speed=1400 rpm; temperature=35° C.; catalyst amount=300 to 500 mg; time=5 hours.

The reaction mixture was sampled and analyzed with an online GC using acetonitrile as internal standard. The catalyst was filtered after each run and recycled. The filtrate was analyzed by ICP to determine extent of metal leaching. The TOF was defined as g ethylene produced/h/g metal (in the catalyst as measured by ICP). Catalyst recycling studies show that once-recycled W-KIT-6 and Ce-TUD-1 catalysts retain activity for 10 hours.

Figure 27:
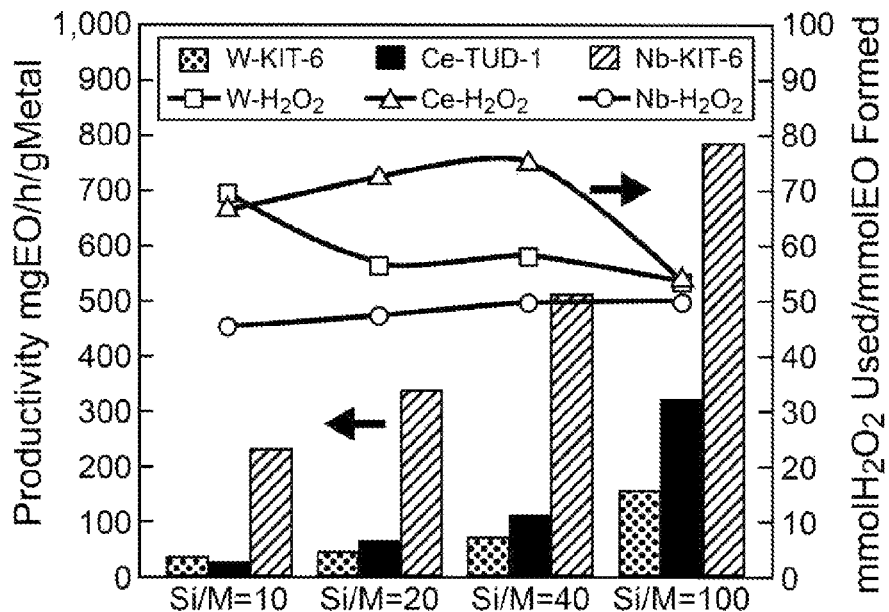
FIG. 27 shows productivity of the mesoporous catalyst of the present invention. The catalyst shows epoxidation activity, but decomposes hydrogen peroxide.

Table 6 lists the productivities (mg EO/h/g active metal), estimated based on weight of EO generated measured by online GC and weight of metal in the catalyst measured by ICP analysis of different catalysts. Under similar operating conditions, niobium catalysts show much higher productivity than tungsten and cerium catalysts. The TOFs of W-KIT-6 (34-152 mgEO/h-gW), W-KIT-5 (13-94 mgEO/h-gW), Nb-KIT-6 (234-794 mgEO/h-gNb), Nb-KIT-5 (273-844 mgEO/h-gNb) and Ce-TUD-1 (22-324 mgEO/h-gCe) catalyst are generally in the same order of magnitude as the conventional silver catalyst (700-4,400 mgEO/h-gAg). The productivities are generally shown in FIG. 27.

TABLE 6

Activities of W-KIT-6, W-KIT-5, Nb-KIT-6, Nb-KIT-5, and Ce-TUD-1 catalysts

| | Productivity mgEO/h-gmetal | | | | |
|---|---|---|---|---|---|
| Si/Metal | W-KIT-6 | W-KIT-5 | Nb-KIT-6 | Nb-KIT-5 | Ce-TUD-1 |
| 10 | 34.4 | 13.6 | 234 | 273 | 22.0 |
| 20 | 43.4 | 23.1 | 340 | 445 | 61.3 |
| 40 | 66.5 | 42.9 | 513 | 602 | 109.7 |
| 100 | 152.6 | 94.8 | 794 | 844 | 324.2 |

Before and after each reaction, aliquots of the reaction mixture were withdrawn to carry out Ceric sulfate titration and Karl Fischer titration to analyze the concentrations of $H_2O_2$ and $H_2O$ respectively.

$H_2O_2$ Determination by Ceric Sulfate Titration:

Hydrogen peroxide content is determined by titrating the standardized ceric sulfate to a pale blue endpoint using ferroin indicator. Ferroin indicator (pink color) is added to the conical flask containing 150 mL of sulfuric acid (5% (v/v)) cooled to below 5° C. This mixture is titrated with ceric sulfate till pale blue and, serves as the baseline. A predetermined amount of sample is added to this solution and swirled to mix. In the presence of excess $H_2SO_4$, $H_2O_2$ oxidizes the ferrous 1,10-phenanthroline to its corresponding ferric derivative giving the solution a pink tinge. This pink color solution is rapidly titrated with ceric sulfate solution. The presence of strong acids enables the reduction of ceric sulfate to cerous sulfate. The free electron needed for this reaction is produced by the oxidation of ferrous 1,10-phenanthroline indicator to its corresponding ferric ion.

$H_2O$ Content Determination by Karl-Fischer Titration:

Volumetric Karl Fischer (KF) titration was used to quantitatively establish the water produced in the epoxidation reaction. The KF titration involves the reaction of iodine with water in an alcoholic solution in the presence of sulfurous acid and base. The KF reaction is pH dependent and performs reliably only in the range of 5 and 7. A predetermined amount of the sample is dissolved in the methanol solvent. The water content of the sample is established by titrating the dissolved sample with hydranal composite 5, a mixture of iodine, sulfur dioxide, and imidazole. The iodine in the titrant reacts with water. The end point of the titration is the detection of free iodine in the solution, recorded by the volumetric indicator. The mass of water formed in the reaction is determined by measuring the water concentration in the liquid phase before and after the reaction.

The results are listed in Table 7 and shown graphically in FIG. 27. There is only a small amount of oxidant being converted to EO. Most of the hydrogen peroxide is decomposing. For example, with W-KIT-6 (Si/W=100), 5 mmol $H_2O_2$ was converted; however, only 0.19 mmol EO was formed. Silylation of the catalysts could reduce the decomposition of hydrogen peroxide.

Example 10

Leaching and Recycle Studies Involving Ethylene Epoxidation Using Catalysts

Figure 28:
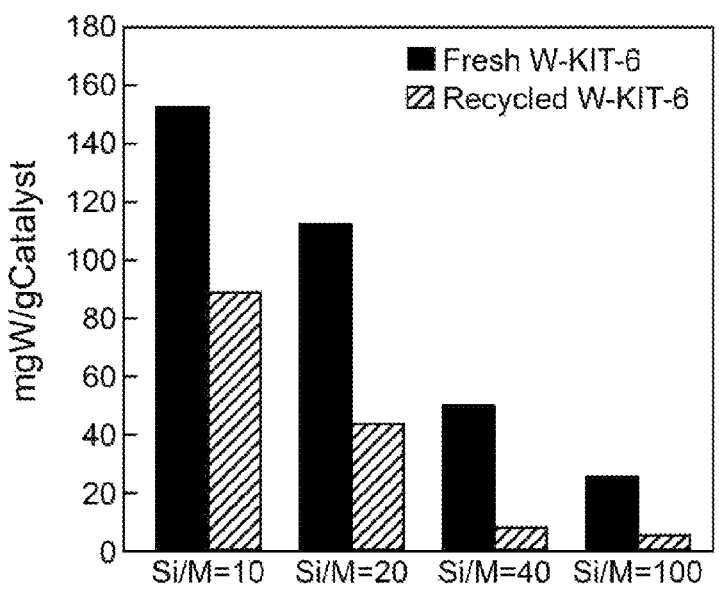
FIGS. 28 and 29 show the recycle studies of W-KIT-6 and Nb-KIT-5 catalysts, respectively, for Si/M=10, 20, 40, and 100 samples.
Figure 29:
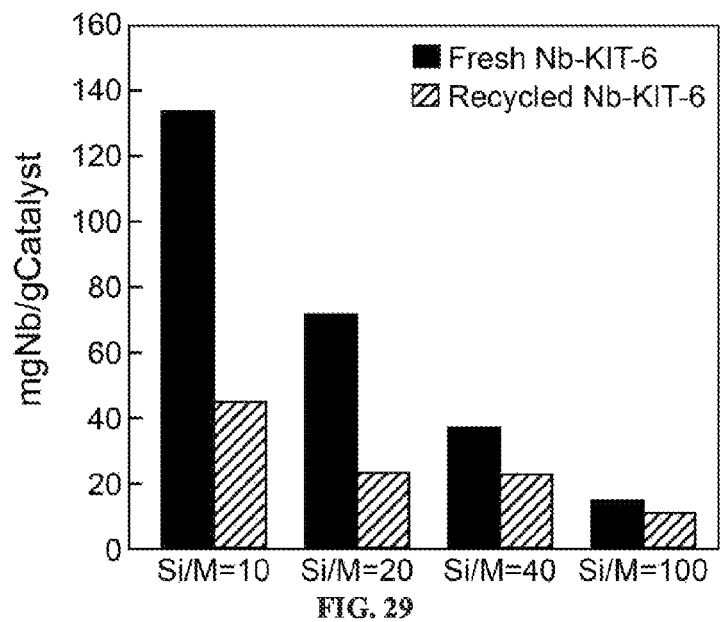

In this example, both fresh and recycled catalysts were digested in a mixture of HF and $H_2SO_4$ solution and ICP-OES analysis was carried out to measure the Si/M ratio. About 30 to 70% metal has leached out of W and Nb catalysts after 5 hours. The leaching percentages for the W-KIT-6 catalysts were 41.1, 60.82, 82.49, and 78.32. However, for Ce-TUD-1 catalyst, no leaching was observed at the end of the 5 hour run. FIGS. 28 and 29 and the following table summarize the data.

TABLE 8

Metal Leaching of W-KIT-6, Nb-KIT-6, Nb-KIT-5, and Ce-TUD-1 Catalysts

| | W-KIT-6 | | Nb-KIT-6 | | Nb-KIT-5 | | Ce-TUD-1 | |
|---|---|---|---|---|---|---|---|---|
| Si/Metal | Leached mgW/gCat | Total mgW/gCat | Leached mgNb/gCat | Total mgNb/gCat | Leached mgNb/gCat | Total mgNb/gCat | Leached mgCe/gCat | Total mgCe/gCat |
| 10 | 62.70 | 152.51 | 45.22 | 134.08 | 49.18 | 122.86 | 0 | 249.9 |
| 20 | 68.80 | 113.12 | 23.27 | 71.86 | 31.52 | 64.15 | 0 | 100.2 |
| 40 | 42.00 | 50.95 | 23.95 | 37.26 | 15.17 | 35.41 | 0 | 49.3 |
| 100 | 20.40 | 26.13 | 11.03 | 15.25 | 6.86 | 14.41 | 0 | 2.02 |

Following a batch run, the catalyst is recovered by filtration and reactivated in a muffle furnace at 500° C. in a flow of air. The calcined catalysts are reused to conduct reactions at the same operating conditions. The recycled catalyst's productivity for the tungsten catalysts (based on the metal content in recycled catalyst) was much higher than the fresh catalysts. The results are listed in Table 9. Even though there is significant leaching of tungsten, the TOFs increased during the 1$^{st}$ recycle. This might due to the leaching of inactive tungsten oxide from the catalysts in preference to the active, framework-incorporated W. However, after the second recycle, the productivity of EU starts to decrease possibly due to leaching of framework incorporated tungsten species. Bulk tungsten oxide and tungsten salts (sodium tungstate and tungstic acid) displayed negligible activity compared to tungsten incorporated mesoporous silica catalysts.

In the case of Ce-TUD-1 (wherein Ce leaching is negligible), a change in the primary oxidation state of cerium ($Ce^{3+}$ to $Ce^{4+}$) is suspected to be the cause for the observed decrease in productivity of the Ce-TUD-1 catalyst. XPS characterization studies are being performed to investigate the $Ce^{3+}/Ce^{4+}$ before and after reaction.

TABLE 7

Hydrogen peroxide decomposition of W-KIT-6, W-KIT-5, Nb-KIT-6, Nb-KIT-5, and Ce-TUD-1 catalysts

| | W-KIT-6 | | | W-KIT-5 | | | Nb-KIT-6 | | | Nb-KIT-5 | | | Ce-TUD-1 | | |
|---|---|---|---|---|---|---|---|---|---|---|---|---|---|---|---|
| Si/M | $H_2O_2$ mmol | $H_2O$ mmol | EO mmol | $H_2O_2$ mmol | $H_2O$ mmol | EO mmol | $H_2O_2$ mmol | $H_2O$ mmol | EO mmol | $H_2O_2$ mmol | $H_2O$ mmol | EO mmol | $H_2O_2$ mmol | $H_2O$ mmol | EO mmol |
| 10 | 12.02 | 11.12 | 0.22 | 12.06 | 13.27 | 0.14 | 20.18 | 21.67 | 1.78 | 28.95 | 27.75 | 1.91 | 15.29 | 14.14 | 0.31 |
| 20 | 7.56 | 6.58 | 0.24 | 10.57 | 9.99 | 0.13 | 20.21 | 18.46 | 1.39 | 20.23 | 19.61 | 1.62 | 20.76 | 23.16 | 0.35 |
| 40 | 7.10 | 6.72 | 0.21 | 7.63 | 7.87 | 0.12 | 20.69 | 21.40 | 1.09 | 18.41 | 20.14 | 1.21 | 19.33 | 21.98 | 0.30 |
| 100 | 5.02 | 5.87 | 0.19 | 6.39 | 6.05 | 0.12 | 13.21 | 12.25 | 0.69 | 17.64 | 18.06 | 0.69 | 9.56 | 11.27 | 0.37 |

TABLE 9

Recycle Study of W-KIT-6 and Ce-TUD-1 Catalysts

| W-KIT-6 | Productivity mgEO/h-gW | Metal content mgW/gCat. | Metal leached out mgW/gCat. | Ce-TUD-1 | Productivity mgEO/h-gCe | Metal content mgCe/gCat | Metal leached out mgCe/gCat. |
|---|---|---|---|---|---|---|---|
| Fresh | 130.5 | 26.43 | 22.68 | Fresh | 61.3 | 100.0 | 0 |
| 1st recycle | 462.6 | 3.75 | 2.13 | 1st recycle | 41.8 | 100.0 | 0.096 (<0.1%) |
| 2nd recycle | 402.6 | 1.62 | 1.35 | 2nd recycle | 25.1 | 99.903 | 0.146 (<0.2%) |

Figure 30:
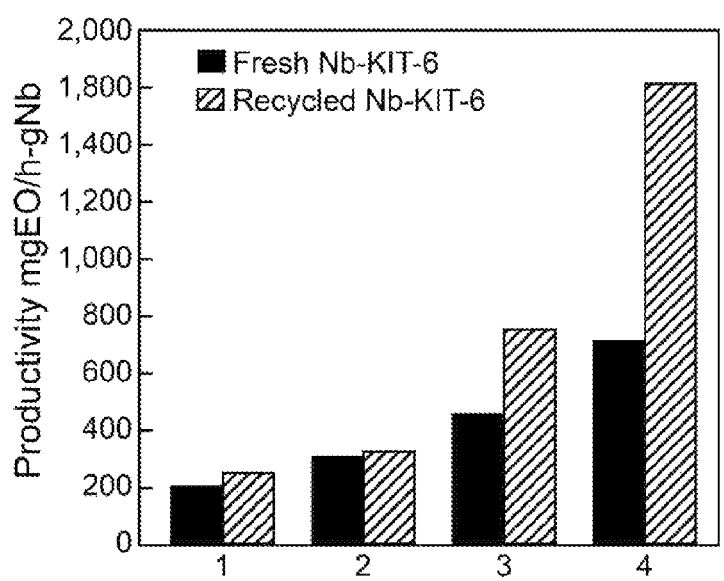
FIGS. 30 and 31 show the recycle studies of Nb-KIT-6 and Nb-KIT-5 catalysts, respectively.
Figure 31:
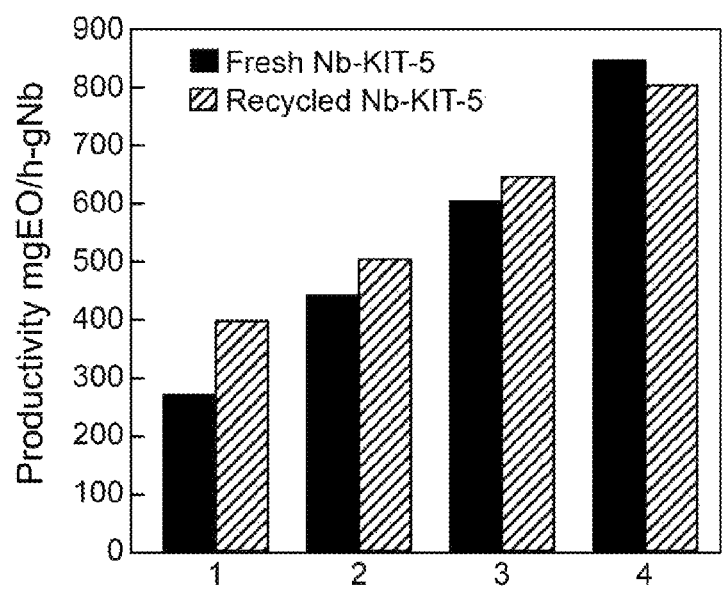

Niobium is an alternative metal which is active for ethylene epoxidation. Nb-based materials showed higher activity compared to W and Ce based catalysts. However, a higher degree of $H_2O_2$ decomposition was noted. Further, about 30%-75% of Nb was leached during the first run. The recycled catalysts displayed activities similar to that of the fresh catalysts as shown in FIGS. 30 and 31. The productivities of the heterogeneous tungsten and cerium-based catalysts (fresh and recycled) are less than either the silver catalyst in the conventional $O_2$-based EO process or the MTO catalyst.

Niobium based catalysts showed excellent selectivity for ethylene oxide (EO) formation (>99%) with a productivity in the same order of magnitude as that of homogeneous Re-based (1.61-4.97 g EO/h/g-Re) and commercial EO process (0.7-4.4 g EO/h/g-Ag). $H_2O_2$ utilization efficiency was very low (roughly 10%) and leaching of niobium (up to 70%) was observed in ICP analysis. However, the productivity (normalized with respect to Nb) was retained in the recycled catalyst.

TABLE 10

Niobium Catalysts EO Experiments

| Catalyst | EO yield mmoles | Productivity mg EO/h/gNb | leaching mg/g Cat | Leaching % | Productivity mg EO/h/gNb |
|---|---|---|---|---|---|
| Nb-KIT-6(100) | 0.69 | 794 | 45 | 34 | 1789 |
| Nb-KIT-6(40) | 1.09 | 513 | 23 | 32 | 844 |
| Nb-KIT-6(20) | 1.39 | 340 | 23 | 62 | 372 |
| Nb-KIT-6(10) | 1.78 | 234 | 11 | 72 | 284 |
| Nb-KIT-5(100) | 0.69 | 844 | 49 | 40 | 804 |
| Nb-KIT-5(40) | 1.21 | 602 | 32 | 49 | 646 |
| Nb-KIT-5(20) | 1.62 | 445 | 15 | 43 | 506 |
| Nb-KIT-5(10) | 1.91 | 273 | 7 | 48 | 396 |
| $Nb_2O_5$ | 0.17 | 9 | | | |
| Niobium oxalate | 0.10 | 21 | | | |

In short, recycled W-KIT-6 shows higher TOF than fresh catalyst. Recycled Nb-KIT-6 has similar TOFs as fresh Nb-KIT-6 catalysts. However, the Ce-TUD-1 deactivated after 1st recycle. For W- and Nb-based silicates, leaching was observed of the active species in the solution. This could be due to solvolysis of M-O-surface bonds by reaction with water and/or polar solvents and solutes. Little if any leaching of cerium was noted with Ce-TUD-1 suggesting that $Ce^{3+}$ sites undergo oxidation to form less reactive $Ce^{4+}$ sites.

Example 11

Silylation Study Involving Ethylene Epoxidation Using Catalysts

In this example, epoxidation of ethylene as an exemplary olefin was evaluated using the silylated exemplary catalysts described herein. More specifically, Nb-40-KIT-5 and Nb-40-KIT-6 were silylated with hexamethyldisilazane (HMDS) and tested for ethylene epoxidation. Previously calcined catalysts (2.5 g) were heated to 120° C. under vacuum for 12 hours. The catalysts were dispersed in 50 ml 5 wt % solution of hexamethyldisilazane in dry toluene under inert atmosphere. The dispersion was stirred for 7 hours in the case of Nb-40-KIT-5, and 24 hours for Nb-40-KIT-6, both at 120° C. The solid was filtered and washed with 200 ml of dry toluene and 400 ml of anhydrous ethanol. For Nb-40-KIT-5, this silylation process was repeated 2 times. For Nb-40-KIT-6, this silylation process was repeated 3 times.

The silylated catalysts were tested for ethylene epoxidation. Calcined catalysts were used as a control. The experimental conditions were as follows: Methanol: 20 g; $H_2O_2$: 8 g; acetonitrile: 0.9 g; catalyst amount: 500 mg; time: 5 hours; temperature: 35° C.; reaction pressure: 50 bar; agitation speed: 1400 rpm. The reaction mixture was sampled and analyzed with an online GC using acetonitrile as internal standard. Table 11 lists the results. Efficiency is defined as mmols of EO being formed per mmol of $H_2O_2$ being consumed. The activity of the silylated catalysts decreased, whereas the utilization efficiency of $H_2O_2$ increased, compared to the calcined catalysts.

TABLE 11

Activity of Silylated Catalysts

| | Nb-KIT-5 | | Nb-KIT-6 | |
|---|---|---|---|---|
| | Calcined 500 mg | Silylated 500 mg | Calcined 500 mg | Silylated 500 mg |
| EO formed mmol | 1.21 | 0.49 | 0.75 | 0.54 |
| $H_2O_2$ converted mmol | 18.41 | 4.54 | 39.00 | 12.88 |
| $H_2O$ formed mmol | 20.14 | 4.57 | 40.45 | 14.24 |
| Efficiency % | 6.6 | 10.8 | 1.9 | 4.2 |

Following a batch run, the catalysts were recovered by filtration and digested in a mixture of HF and $H_2SO_4$ solutions and ICP-OES analysis was carried out to measure the Si/M ratio. The results are listed in Table 12. About 15-25% of Nb leached out of the silylated catalysts after 5 hours, which is less than the approximately 36-43% of Nb that leached out of the calcined but unsilylated catalysts under similar conditions. In addition, silylation of the catalysts resulted in a small amount of silicon leaching, which did not occur with the calcined but unsilylated catalysts.

TABLE 12

Leaching Study of Silylated Catalysts

| | Silylated Nb-40-KIT-5 | Calcined Nb-40-KIT-5 | Silylated Nb-40-KIT-6 | Calcined Nb-40-KIT-6 |
|---|---|---|---|---|
| Nb content mgNb/0.5 g Catalyst | 16.53 | 17.71 | 14.37 | 16.78 |

TABLE 12-continued

Leaching Study of Silylated Catalysts

|  | Silylated Nb-40-KIT-5 | Calcined Nb-40-KIT-5 | Silylated Nb-40-KIT-6 | Calcined Nb-40-KIT-6 |
|---|---|---|---|---|
| Nb Leaching mgNb/0.5 g Catalyst | 2.60 | 7.59 | 3.53 | 6.05 |
| Leaching Percentage % | 15.73 | 42.84 | 24.57 | 36.05 |
| Silicon content mg Si/0.5 g Catalyst | 195.14 | 214.09 | 171.61 | 172.3 |
| Silicon Leaching mg Si/0.5 g Catalyst | 13.77 | 0.00 | 15.64 | 0.00 |
| Leaching Percentage % | 7.06 | 0.00 | 9.11 | 0.00 |

While the invention has been described and illustrated hereinabove with reference to various exemplary embodiments, it should be understood that the invention is not limited to the methodologies or configurations of these embodiments. In addition, although the exemplary embodiments are described as embodying several different inventive features, one skilled in the art will appreciate that any one of these features could be implemented without the others in accordance with the invention. Therefore, the invention is not to be limited to the exemplary embodiments described and illustrated hereinabove, except insofar as such limitations are included in the following claims.

We claim:

1. A process for epoxidizing an olefin comprising:
contacting an olefin selected from the group consisting of ethylene and propylene with hydrogen peroxide in the presence of an insoluble oxidation catalyst in a solvent system comprising an organic water-miscible solvent to form ethylene oxide or propylene oxide such that there is no detectable carbon dioxide as a byproduct, and
wherein said insoluble oxidation catalyst comprises a metal selected from the group consisting of tungsten, cerium, and niobium, and wherein said metal is directly incorporated within a solid mesoporous silicate support.

2. The process of claim 1 wherein said olefin is ethylene.

3. The process of claim 1 wherein said organic water miscible solvent is selected from the group consisting of a $C_1$ to $C_4$ alcohol.

4. The process of claim 1 wherein said solvent system comprises methanol and water.

5. The process of claim 1 wherein said wherein said epoxidizing process occurs at a temperature of about 20 to 40° C.

6. The process of claim 1 wherein said epoxidizing process occurs at a pressure of about 40 to 60 bar.

7. The process of claim 1 wherein said catalyst comprises said metal directly incorporated into a mesoporous silicate selected from the group consisting of KIT series, TUD series, and M41S series silicates.

8. The process of claim 1 wherein said solid mesoporous silicate support comprises an amorphous mesoporous silicate.

9. The process of claim 1 wherein said solid mesoporous silicate support comprises an ordered mesoporous silicate.

10. The process of claim 1 wherein said catalyst has a metal to mesoporous silicate ratio of about 5 to 150.

11. The process of claim 1 wherein said catalyst comprises tungsten and said catalyst has a specific surface area of about 500 to 1500 $m^2/g$.

12. The process of claim 1 wherein said catalyst comprises tungsten and said catalyst has a pore volume of about 0.8 to 1.8 cc/g.

13. The process of claim 1 wherein said catalyst comprises tungsten and said catalyst has a average pore diameter of about 2 to 10 nm.

14. The process of claim 1 wherein said catalyst comprises cerium and said catalyst has a specific surface area of about 100 to 1000 $m^2/g$.

15. The process of claim 1 wherein said catalyst comprises cerium and said catalyst has a pore volume of about 0.5 to 1.5 cc/g.

16. The process of claim 1 wherein said catalyst comprises cerium and said catalyst has a average pore diameter of about 2 to 20 nm.

17. The process of claim 1 wherein said catalyst comprises niobium and said catalyst has a specific surface area of about 500 to 1500 $m^2/g$.

18. The process of claim 1 wherein said catalyst comprises niobium and said catalyst has a pore volume of about 0.5 to 1.8 cc/g.

19. The process of claim 1 wherein said catalyst comprises niobium and said catalyst has a average pore diameter of about 5 to 15 nm.

20. The process of claim 1 wherein said metal is tungsten and said tungsten is in the form of lithium tungstate, sodium tungstate, potassium tungstate, cesium tungstate, magnesium tungstate, calcium tungstate, barium tungstate, ammonium tungstate, cadmium tungstate, cerium tungstate, cobalt tungstate, copper tungstate, silver tungstate, or combinations thereof.

21. The process of claim 1 wherein said metal is cerium and said cerium is in the form of cerium nitrate, cerium sulphate, cerium acetate, cerium chloride, ceric ammonium nitrate, or combinations thereof.

22. The process of claim 1 wherein said metal is niobium and said niobium is in the form of niobium chloride, niobium oxychloride, niobium fluoride, niobium bromide, niobium oxalate, or combinations thereof.

23. The process of claim 1 further comprising the step of recycling said oxidation catalyst to said contacting step.

24. A process for epoxidizing an olefin comprising:
contacting an olefin with an oxidant in the presence of an insoluble oxidation catalyst in a solvent system comprising an organic water-miscible solvent to form an alkylene oxide;
wherein said insoluble oxidation catalyst comprises a metal selected from the group consisting of tungsten, cerium, and niobium, and wherein said metal is directly incorporated within a solid mesoporous silicate support selected from the group consisting of KIT-5, KIT-6, and TUD-1.

25. The process of claim 24 wherein said olefin is selected from the group consisting of ethylene, butenes, butadiene, pentenes, isoprene, 1-hexene, 3-hexene, 1-heptene, 1-octene, diisobutylene, 1-nonene, their double-bond positional isomers.

26. The process of claim 24 wherein said organic water miscible solvent is selected from the group consisting of a $C_1$ to $C_4$ alcohol.

27. The process of claim 24 wherein said wherein said epoxidizing process occurs at a temperature of about 20 to 40° C. and a pressure of about 40 to 60 bar.

28. The process of claim 24 wherein said catalyst has a metal to mesoporous silicate ratio of about 5 to 150.

29. The process of claim 24 wherein said catalyst has a specific surface area of about 100 to 1500 m²/g, a pore volume of about 0.5 to 1.8 cc/g, and an average pore diameter of about 2 to 20 nm.

30. The process of claim 24 wherein said metal is selected from the group consisting of lithium tungstate, sodium tungstate, potassium tungstate, cesium tungstate, magnesium tungstate, calcium tungstate, barium tungstate, ammonium tungstate, cadmium tungstate, cerium tungstate, cobalt tungstate, copper tungstate, silver tungstate, cerium nitrate, cerium sulphate, cerium acetate, cerium chloride, ceric ammonium nitrate, niobium chloride, niobium oxychloride, niobium fluoride, niobium bromide, and niobium oxalate.

31. The process of claim 1 further comprising the step of recycling said oxidation catalyst to said contacting step.

* * * * *